United States Patent
Whitten et al.

(10) Patent No.: US 9,625,401 B2
(45) Date of Patent: Apr. 18, 2017

(54) MOLECULAR ANALYSIS USING MICRO ELECTRO-MECHANICAL SENSOR DEVICES

(71) Applicant: Nevada Nanotech Systems, Inc., Sparks, NV (US)

(72) Inventors: Ralph G. Whitten, Truckee, CA (US); Jesse D. Adams, Reno, NV (US); David R. Halbert, Placerville, CA (US); Joseph P. Barrus, Reno, NV (US); Benjamin S. Rogers, Reno, NV (US)

(73) Assignee: Nevada Nanotech Systems Inc., Sparks, NV (US)

(*) Notice: Subject to any disclaimer, the term of this patent is extended or adjusted under 35 U.S.C. 154(b) by 44 days.

(21) Appl. No.: 14/425,423

(22) PCT Filed: Sep. 13, 2013

(86) PCT No.: PCT/US2013/059720
§ 371 (c)(1),
(2) Date: Mar. 3, 2015

(87) PCT Pub. No.: WO2014/043508
PCT Pub. Date: Mar. 20, 2014

(65) Prior Publication Data
US 2015/0253265 A1   Sep. 10, 2015

Related U.S. Application Data

(60) Provisional application No. 61/700,729, filed on Sep. 13, 2012.

(51) Int. Cl.
*G01N 27/00* (2006.01)
*G01N 25/48* (2006.01)
*G01N 25/20* (2006.01)
*G01N 33/543* (2006.01)

(52) U.S. Cl.
CPC ......... *G01N 25/4826* (2013.01); *G01N 25/20* (2013.01); *G01N 33/54373* (2013.01)

(58) Field of Classification Search
CPC .................... G01N 33/0031; G01N 29/022
USPC ............................. 422/82.02, 82.01
See application file for complete search history.

(56) References Cited

U.S. PATENT DOCUMENTS

| | | | |
|---|---|---|---|
| 4,848,921 A | 7/1989 | Kunze | |
| 5,439,291 A | 8/1995 | Reading | |
| 5,819,842 A * | 10/1998 | Potter | B01L 7/54 165/206 |

(Continued)

OTHER PUBLICATIONS

International Preliminary Report on Patentability for International Application No. PCT/US2013/059720, dated Mar. 17, 2015, 8 pages.

(Continued)

*Primary Examiner* — Natalia Levkovich
(74) *Attorney, Agent, or Firm* — TraskBritt

(57) ABSTRACT

Analysis instruments and sensors, particularly micro-electro mechanical sensor (MEMS) devices, for molecular analysis of chemicals and other materials, including, for example, polymers, drugs, nanomaterials, biological samples including proteins, and environmental samples including water suspected of contamination, and the like in vapor, liquid, and/or solid form.

20 Claims, 20 Drawing Sheets

(56) References Cited

U.S. PATENT DOCUMENTS

| | | | |
|---|---|---|---|
| 6,146,013 | A | 11/2000 | Huetter et al. |
| 6,331,074 | B1 | 12/2001 | Kimura |
| 7,665,889 | B2 | 2/2010 | Kjoller et al. |
| 7,909,505 | B2 | 3/2011 | Alexandrov et al. |
| 8,524,501 | B2 | 9/2013 | Adams |
| 2006/0062272 | A1 | 3/2006 | Grudin et al. |
| 2006/0254345 | A1 | 11/2006 | King et al. |
| 2008/0085212 | A1* | 4/2008 | Adams ............ G01N 29/036 422/50 |
| 2012/0092175 | A1 | 4/2012 | Adams et al. |

OTHER PUBLICATIONS

International Search Report for International Application No. PCT/US2013/059720, dated Nov. 18, 2013, 6 pages.

International Written Opinion of the International Searching Authority for International Application No. PCT/US2013/059720, dated Nov. 18, 2013, 7 pages.

Guenther G. et al, "High-Temperature Chip Calorimeter with Atmosphere Control," THERMOCHIMICA ACTA, vol. 522, No. 1, pp. 77-85 (Mar. 31, 2011).

Jungchul Lee et al., "Differential Scanning Calorimeter Based on Suspended Membrane Single Crystal Silicon Microhotplate," Journal of Microelectromechanical Systems, IEEE Service Center, U.S., vol. 17, No. 6 (Dec. 1, 2008).

Privorotskaya, N. L., "Silicon Microcantilever Hotplates with High Temperature Uniformity," Sensors and Actuators A, Elsevier Sequoia S.A., Lausanne, CH, vol. 152, No. 2, pp. 160-167 (Jun. 18, 2009).

Olson, E.A. et al., "Scanning Calorimeter for Nanoliter-Scale Liquid Samples," Applied Physics Letters, American Institute of Physics, Mellville, NY, US, vol. 77, No. 17, pp. 2671-2673 (Oct. 23, 2000).

\* cited by examiner

MOLECULAR ANALYSIS USING MICRO ELECTRO-MECHANICAL SENSOR DEVICES

FIELD OF THE INVENTION

This invention relates to analysis instruments and sensors, particularly micro-electro mechanical sensor (MEMS) devices, for molecular analysis of chemicals and other materials, including, for example, polymers, drugs, nanomaterials, biological samples including proteins, and environmental samples including water suspected of contamination, and the like in vapor, liquid, and/or solid form.

BACKGROUND

Molecular analysis presents many challenges depending upon the specific application and nature of the material being analyzed. In many cases, a portable analysis instrument is very useful as well as one of low cost, however, traditional instruments for high accuracy liquid analysis, for example, tend to be larger laboratory instruments, which by their nature are also expensive. Traditional laboratory instruments also tend to require relatively large sample amounts, and for instruments using thermal analysis methods, a relatively long analysis time, which limits throughput in some applications.

With regard to different thermal analysis techniques, a MEMS-based solution could address a number of existing problems. Some popular thermoanalytical techniques include Differential Thermal Analysis (DTA) and Differential Scanning calorimetry (DSC). In DTA, the material under study and a reference material are made to undergo identical thermal cycles, while recording any temperature difference between sample and reference. This differential temperature is then plotted against time, or against temperature (a DTA curve or thermogram). Changes in the sample, for example, enthalpy changes or specific heat changes, can be detected relative to the inert reference. Thus, a DTA curve provides data on the transformations that have occurred such as glass transitions, crystallization, melting, and sublimation.

When applied to chemical sensors and analytical instruments, a sample of an analyte (or a combination of analytes) is captured on a primary sensor probe or element and then heated in a controlled manner. Variations in the measured temperature signal from the probe are caused by adsorbed heat due to a combination of melting, evaporation, and decomposition or other phase changes, which can produce a distinct temperature profile for each analyte when compared with a signal from an identical probe that has no analytes present and that is heated in an identical manner. Subtracting the reference response from the signal given off by the primary probe produces the data of interest as a result. Sometimes instead of having no material, the reference probe may analyze an amount of an inert or neutral substance, such as a buffer solution in the case of some forms of liquid analysis.

Another form of calorimetry called "differential scanning calorimetry" or "DSC" is similar to DTA. DSC is a thermoanalytical technique in which the amount of heat required to increase the temperature of a sample is measured and compared to a reference as a function of temperature. Both the sample and reference are maintained at nearly the same temperature throughout the experiment. Generally, the temperature program for a DSC analysis is designed such that the sample holder temperature increases linearly as a function of time. The reference sample should have a well-defined heat capacity over the range of temperatures to be scanned. The term DSC was coined to describe an instrument that measures energy directly and allows precise measurements of heat capacity.

The basic principle underlying this technique is that when the sample undergoes a physical transformation, such as any type of phase transition, more or less heat will need to flow to it compared to the reference to maintain both at the same temperature. Whether less or more heat must flow to the sample depends on whether the transformation process is exothermic or endothermic. For example, in many cases, as a solid sample melts to a liquid, it will require more heat flowing to the sample to increase its temperature at the same rate as the reference. This is due to the absorption of heat by the sample as it undergoes an endothermic phase transition from solid to liquid. Likewise, as the sample undergoes an exothermic processes (such as crystallization), less heat can be required to raise the sample temperature. By observing the difference in heat flow between the sample and reference, differential scanning calorimeters are able to measure the amount of heat absorbed or released during such transitions. DSC may also be used to observe more subtle phase changes, such as glass transitions. DSC is widely used in industrial settings as a quality control instrument due to its applicability in evaluating sample purity and for studying polymer curing. In the field of biology, DSC is often used to study denaturing of samples such as protein unfolding, and the unbinding of molecules such as the unbinding of antibody-antigen pairs or the uncoupling of DNA strands.

Where multiple sensor probes or transducers are included in a single miniature array such as in a MEMS array constructed using semiconductor fabrication techniques, isolation of a reference probe can sometimes require additional size, complexity, and cost in order to properly isolate the reference probe. Traditional DTA and DSC methodologies of utilizing separate primary and reference probes have the additional negative characteristic where any subtle physical differences between the primary measurement probe and the reference probe may introduce errors into the DTA or DSC measurement result. For applications where a separate reference cell is definitely required, micro-fabrication will help to reduce variation between a sample cell and a reference cell and also reduce the cost of the reference cell, due to the small size and the simultaneous fabrication of the sample cell and the reference cell.

Accordingly, there is a need for new and/or improved MEMS devices and methods for molecular analysis of chemicals and other materials that can overcome the aforementioned drawbacks.

SUMMARY

A MEMS-based analysis solution can provide both small size and low cost, while having the additional benefit of being able to analyze very small samples of analyte material and do so more quickly than traditional analysis instruments. In some applications, such as the analysis of nanomaterials or biological samples, it may happen, especially in research environments, that only a very small amount of material is available for analysis. Again, a MEMS-based solution by nature of the small size of a typical MEMS sensor element, can frequently analyze much smaller sample sizes than a traditional laboratory analysis instrument.

A common technique used in the analysis of both biological and non-biological materials is thermal analysis, and, in particular, techniques such as Differential Thermal Analysis (DTA) and Differential Scanning calorimetry (DSC), as discussed above. Historically, these two methods are typically implemented in laboratory instruments using a relatively conventional oven subsystem. When implemented with a MEMS sensor element, not only can very small sample sizes be handled, a very high thermal ramp rate can be accomplished when the element and a sample are heated during an analysis cycle. This has the advantage of providing a relatively high signal output even for extremely small, nanogram-sized samples. Alternatively, this rapid analysis can provide a higher signal-to-noise ratio, which can reduce the cost and complexity of the measurement equipment.

According to the invention, thermal analysis methods can be carried out on a single sensor element, a pair of sensor elements, or a large array of sensor elements, a large array being useful for certain biological analysis applications. DSC and DTA may be performed with a pair of sensor elements analyzing an analyte and a reference for differential analysis. Alternatively, a single sensor element may provide reference data for comparison with data results from a plurality of analyte sensor elements. In yet another alternative embodiment, reference and analyte analysis cycles may be performed on the same sensor element, with analysis cycles separated in time.

According to one embodiment of the invention, temporally separated sample and reference measurements for either DTA or DSC are implemented by ramping the temperature for the same sensor probe multiple times in sequence and using one or more of the ramps as references for another ramp, for which the sensor probe was loaded with analyte, all with the same sensor element. This method is different than conventional approaches where a second and isolated reference device is utilized.

When implementing DTA or DSC with a MEMS-based microsensor array having multiple sensor elements to analyze a single analyte sample, it can be advantageous to have all of the probes relatively close together such that an analyte stream (vapor, liquid, and/or aerosol/particle) will have a maximum probability of placing sufficient numbers of target analyte molecules on each sensor probe. Given this, in some scenarios it becomes difficult to have one of the probes of the array physically isolated from the others such that it can serve the purpose of a reference sensor probe, per the conventional DTA or DSC paradigm. A sensor array could be replicated in another physical location in order to provide an isolated reference probe, however, that would be more expensive and space-consumptive when only one sample is being analyzed. A unique solution, according to one embodiment of the present invention, is a sequential analysis technique where the same sensor probe is utilized for both measurements, the measurement with analyte present and the measurement with analyte not present, and then the two measurements are compared in order to derive the information required for a DTA or DSC analysis. When an array of sensor elements is intended to analyze multiple samples, this sequential technique can reduce or eliminate the number of additional sensor elements required for reference measurements.

Since according to the method just described, the same probe is used for both the primary heating cycle and the reference heating cycle, it can be desirable that the reference heating cycle finish with the probe free of analyte (essentially cleaned as a result of the primary heating cycle), and that whatever clean state the probe ends up in is consistent from one test to the next, such as where a sensor element is to be re-used for multiple analysis cycles. The primary heat cycle starts with some amount of analyte on the sensor probe, which may embody a microcantilever, a microbridge, or a cluster of elements acting in unison. Typically, some amount of analyte may remain after the primary heat cycle and thus the probe may not be fully clean. If the second heat cycle does not start with a clean probe, then the "differential" information may not be as accurate as desired. Therefore, a third heat cycle can be performed and is used in conjunction with the second heat cycle to provide a reference for the "differential" analysis. And at the same time, the third cycle data can be compared with that for the second cycle data so that the system can tell just how clean the sensor probe really is. If there is a noticeable difference between the second cycle data and third cycle data, then the system may opt to run a fourth heating cycle, etc. Thus, it may be decided that the system performs "n" cycles in order to determine that the proper level of cleanliness has been reached, and therefore provide the most consistent measurements from test-to-test while using only one probe.

In another embodiment, a sensor device for analysis of an analyte is provided, which includes an array of a plurality of sensor cells arranged in at least one row and in at least one column. Each sensor cell is configured to receive analyte for analysis of the analyte and includes a heating element and a temperature sensor element. The heating element is configured to heat the sensor cell and/or the analyte and the temperature sensor element is configured to sense a temperature response of the heated sensor cell and/or the analyte.

In another embodiment, a method of analyzing an analyte is provided, which includes receiving an analyte in a sensor cell in a sensor device. Then, the sensor cell with the analyte and/or the analyte in the sensor cell is heated in a controlled manner via a heating element. A response is sensed via a temperature sensor element from the heated sensor cell and/or the analyte during heating. The analyte is analyzed by comparing the sensed response to a sensed response from a reference sensor cell that has been heated in the same controlled manner. In another example, the method includes receiving an analyte in one of a plurality of sensor cells in an array of a sensor device. In another example, the analyte is analyzed by comparing a sensed temperature response of the sensor cell and/or the analyte to a sensed temperature response from a reference sensor cell that has been heated in the same controlled manner. In yet another example, the analyte is analyzed by comparing sensed power required to heat the sensor cell and/or the analyte to sensed power required to heat a reference sensor cell that has been heated in the same controlled manner.

In yet another embodiment, a method of analyzing an analyte is provided, which includes receiving an analyte in a plurality of sensor cells in an array of a sensor device. Then, a plurality of sensor cells with the analyte and/or the analyte in the sensor cells is heated in a controlled manner via corresponding heating elements. A response is sensed via corresponding temperature sensor elements from the heated sensor cell and/or the analyte during heating. And, the analyte is analyzed by comparing the sensed responses to a sensed response from the reference sensor cell that has been heated in the same controlled manner. In one example, the analyte is analyzed by comparing sensed temperature responses of the sensor cells and/or the analyte to a sensed temperature response from a reference sensor cell that has been heated in the same controlled manner. In yet another example, the analyte is analyzed by comparing sensed power required to heat the sensor cells and/or the analyte to sensed power required to heat a reference sensor cell that has been heated in the same controlled manner.

BRIEF DESCRIPTION OF THE DRAWINGS

The accompanying drawings, which are incorporated in and constitute a part of this specification, illustrate embodiments of the invention and, with a detailed description of the embodiments given below, serve to explain the principles of the invention.

DETAILED DESCRIPTION

While a number of MEMS-based sensor elements or devices are known, some of the most sensitive and effective are microcantilevers and microbridge structures. Microcantilever structures can take the form of an array of conventional "diving board" structures, or alternatively, a new configuration described herein as a "radially oriented cantilever cluster." Suitable microcantilever structures for use herein, including conventional "diving board" type cantilever structures, are disclosed in U.S. Pat. No. 8,524,501, the contents of which is expressly incorporated by reference herein in its entirety.

Matrix Arrays of MEMS Sensor Cells for Liquid Analysis

Some liquid analysis applications, such as biological analysis, have existing conventions in the laboratory environment for how samples are organized and processed to determine their characteristics and constituents. One of these conventions is that of utilizing multi-cell sample cartridges, which contain a matrix of wells wherein different samples may be placed. A common size for this matrix contains 96 wells or cells where each may contain a different analyte sample, typically in solution with some form of buffer liquid. Other matrix sizes are also common. Another common analysis mode is for the matrix to contain a number of different samples but with repeats of each sample, for example, triplicate testing in which each sample is tested three times to repeat each experiment. For thermal analysis applications where a reference analysis cycle is compared with an analysis cycle for a specific analyte, there may also be cartridges containing solutions of buffer liquid that have no form of analyte, these being sometimes matched with a specific analyte solution and used in a corresponding reference analysis cycle.

Figure 1:
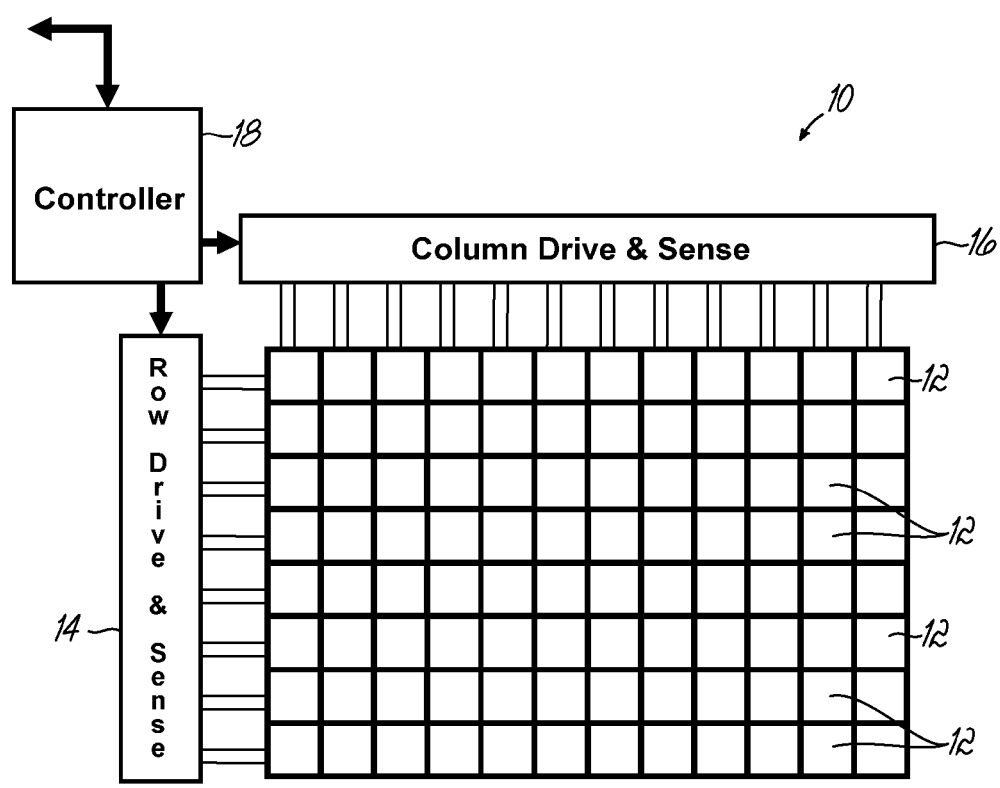
FIG. 1 illustrates a 96-cell sensor array with drive and sense electronics included for both the rows and columns of the cell matrix in accordance with an embodiment of the invention.

For applications where only a 96-cell sensor array 10 is required, the sensor array 10 shown in FIG. 1 may be utilized. Each sensor well or cell 12, which together define a cell matrix of rows and columns, can contain heating and sensing elements (not shown), which are described and shown further hereinbelow (see, e.g., FIGS. 3-6A) and may be separate or may be one and the same element, i.e., define a unitary element. When heating and sensing elements are one and the same, temperature may be sensed by observing the resistance of the element during the analysis cycle, or alternatively, by intermittently applying a heating pulse and then measuring the resistance of the heated element after a brief relaxation period, as more fully described below.

Figure 20:
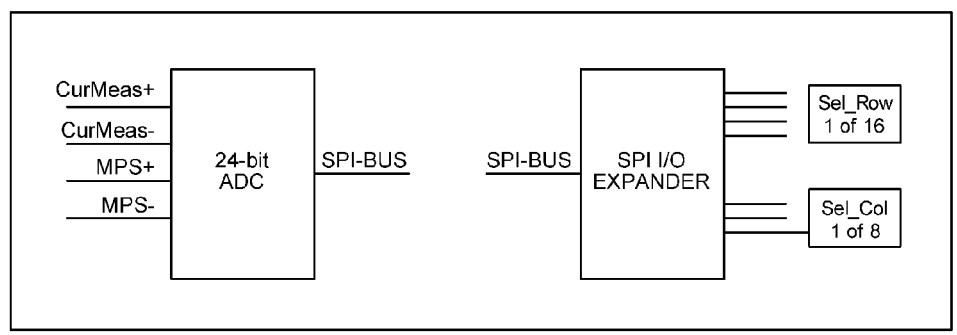
FIG. 20 is a schematic diagram of a high-resolution 24-bit ADC that is connected to the output of the differential amplifier of FIG. 19.
Figure 23:
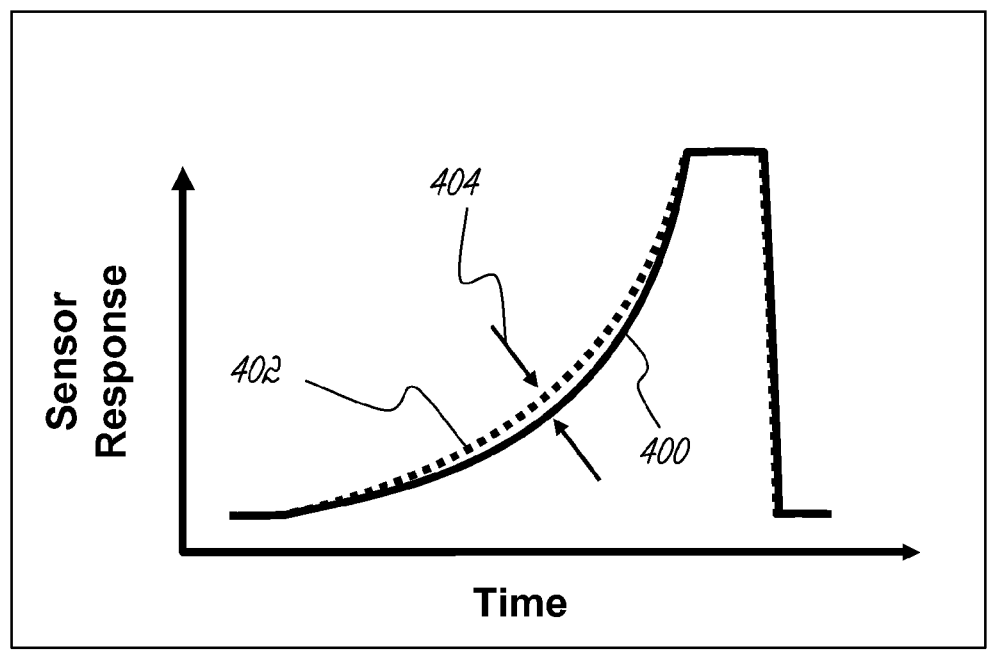
FIG. 23 is a graph showing result curves for a sequential differential analysis performing DTA.

As further shown in FIG. 1, respective row and column drive and sense electronics 14 and 16 for applying power and sensing the temperature of the cells 12 are separately included for the rows and columns of the cell matrix, and the analytical processing of samples in the sensor array 10 may be done one sensor cell 12 at a time, or alternatively, an entire row or an entire column may be analyzed simultaneously. When the row and column drive and sense electronics 14, 16, which interface directly with the cell matrix of the sensor array 10, are packaged in close proximity with the cell matrix, it is useful to have a controller device 18 as shown in FIG. 1, which interfaces with the drive and sense electronics 14, 16 for selecting the desired cell(s) 12 for analysis, while presenting a relatively small number of signal paths to system components, including current sources, operational amplifiers, and analog-to-digital converters not closely associated with the cell matrix. The controller device 18 can be, for example, an I/O Expander controlled by a processor by an SPI bus, as shown in FIG. 20, to execute one or more instructions to perform one or more operations consistent with embodiments of the invention. The sensed data, as shown in FIG. 23, for example, and discussed further herein, can be processed by chemometric software algorithms, as is well known in the art. This arrangement minimizes the amount of wiring required to connect to a cartridge (not shown) containing the cell sensor array 10 and, by utilizing a low-cost controller device 18, the entire cost of the cartridge including the controller 18, the drive and sense electronics 14, 16, and the cell matrix can be minimized. For applications where it is desirable to use the cartridge one time only and then dispose or archive the cartridge after analysis, such a low-cost solution is highly desirable.

Figure 18:
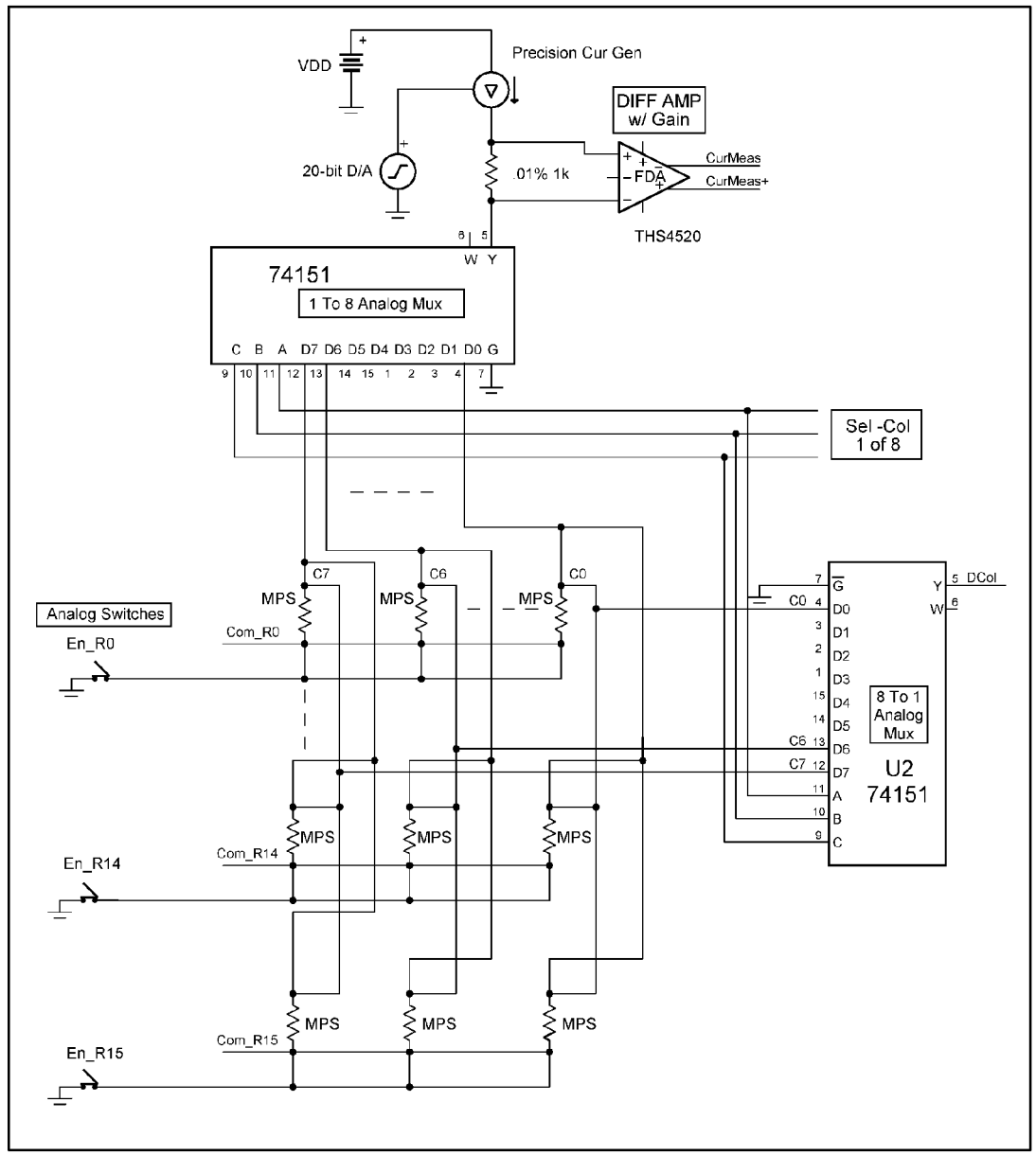
FIG. 18 is a schematic diagram of a circuit for driving and sensing an array of cells where thermal analysis is performed by heating and temperature sensing using a common sensor element.
Figure 19:
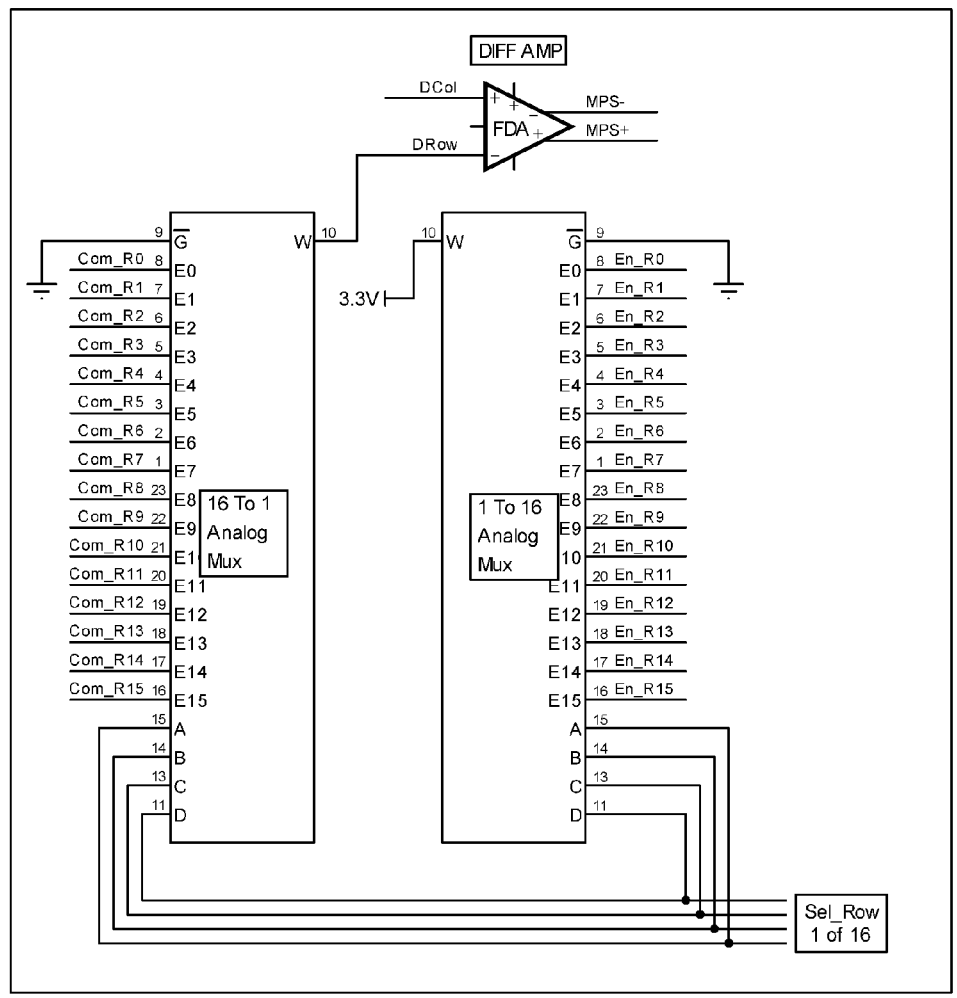
FIG. 19 a schematic diagram showing multiplexers used for controlling both drive selection and sensing selection in the circuit of FIG. 18.

In operation, power is applied to the heating element(s) of a desired cell(s) 12 in the sensor array 10, as shown by example in FIG. 18, in which the current from a precision current source is directed to a particular column of the sensor array 10. A specific cell(s) 12 can be selected in that column by controlling the row driver circuitry with a multiplexer to complete the electrical circuit of the current source, as shown in FIG. 19. The temperature from each cell can be monitored as shown in FIGS. 18 and 19. By monitoring the temperature, a control algorithm can adjust the power applied to the cell to maintain the desired temperature ramp heat cycle, as is well known in the art. The arrows in FIG. 1 represent the electrical connections shown in FIG. 20, for example.

The sensed data can be collected, stored, and analyzed, such as by a common computer system. Along with an input/output ("I/O") interface, each computing system can generally include a display and external devices. The I/O interface may be configured to receive data from the display and data from the external devices that is communicated to a processor and may be configured to output data from the processor to the display and external devices. The display may be, for example, a computer monitor or a screen on a mobile device. Alternatively, the display may be a touch screen that not only functions to permit a user to receive and view output data, but also functions to permit the user to input data with, for example, an onscreen virtual keyboard. The external devices may include, for example, additional user input devices such as a keyboard, a keypad, a mouse, a microphone, etc., and additional user output devices such as speakers, etc. The computer system may also include a network adapter, such as a network interface card or a transceiver, that supplies the physical connection with a network and that is configured to transmit and receive data over the network. External devices also can be, for example, the SPI I/O expander shown in FIG. 20 that receives data from the computer system to control the sensor system or the 24-bit analog-to-digital converter (ADC) that provides data from the sensor system to the computer system for analysis.

Figure 21:
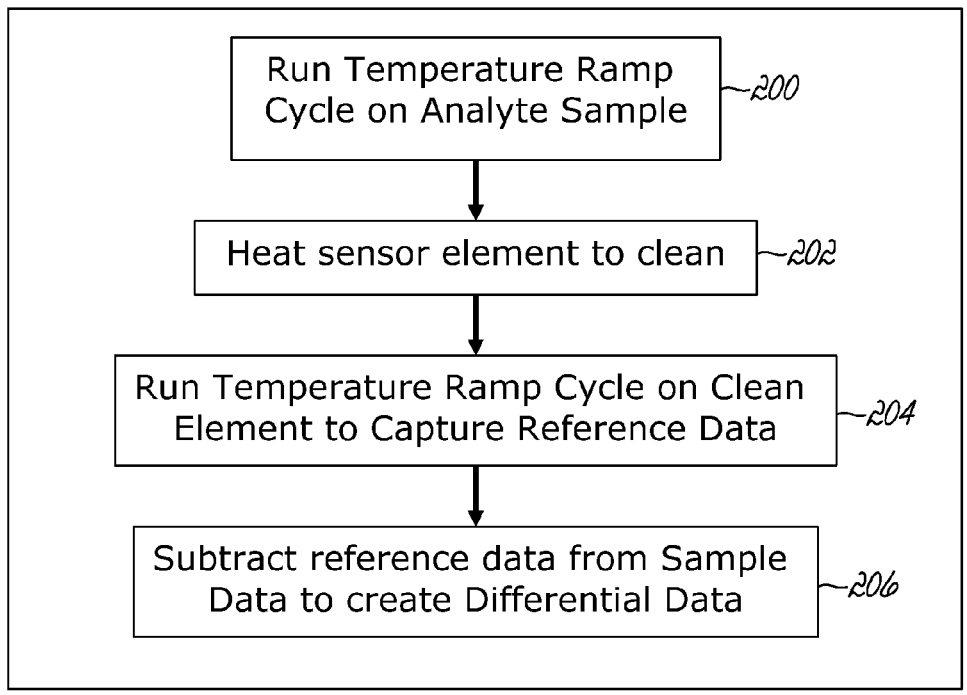
FIG. 21 is a flowchart illustrating a temporally separated differential analysis method according to one embodiment of the invention that can be utilized for DTA or DSC analysis.
Figure 22:
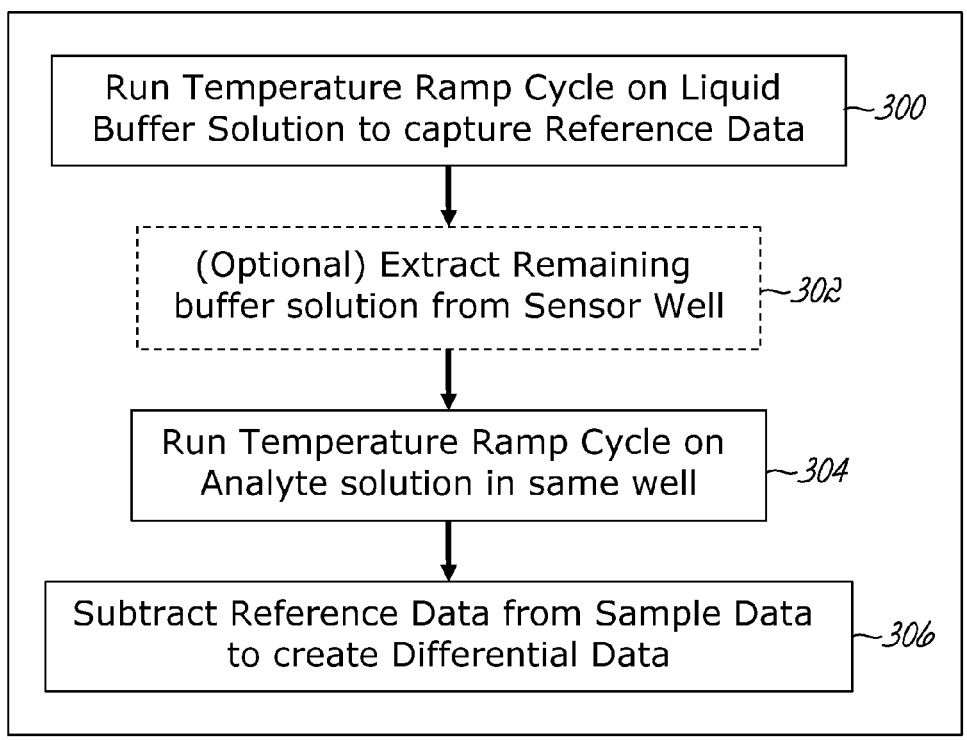
FIG. 22 is a flowchart illustrating a temporally separated differential analysis method according to another embodiment of the invention that can be utilized for DTA or DSC analysis.

In one embodiment of the invention, analysis cycles and reference cycles for differential analysis measurements are performed sequentially by repeated temperature ramp heat cycles on the same cell 12, as shown in FIGS. 21 and 22 and described hereinbelow, and such a 96-cell sensor array 10 would be sufficient for analyzing 96 analyte samples. If additional cells 12 are required for performing reference analysis cycles simultaneous with analyte analysis cycles, additional rows or columns may be added to the cell matrix of FIG. 1. For some applications, it may be adequate for a single reference cell to support multiple reference analysis cycles and thereby be used with a plurality of analysis sensor cells. For applications where this is the case, adding an additional row or an additional column to a 96-cell array may be adequate.

Figure 2:
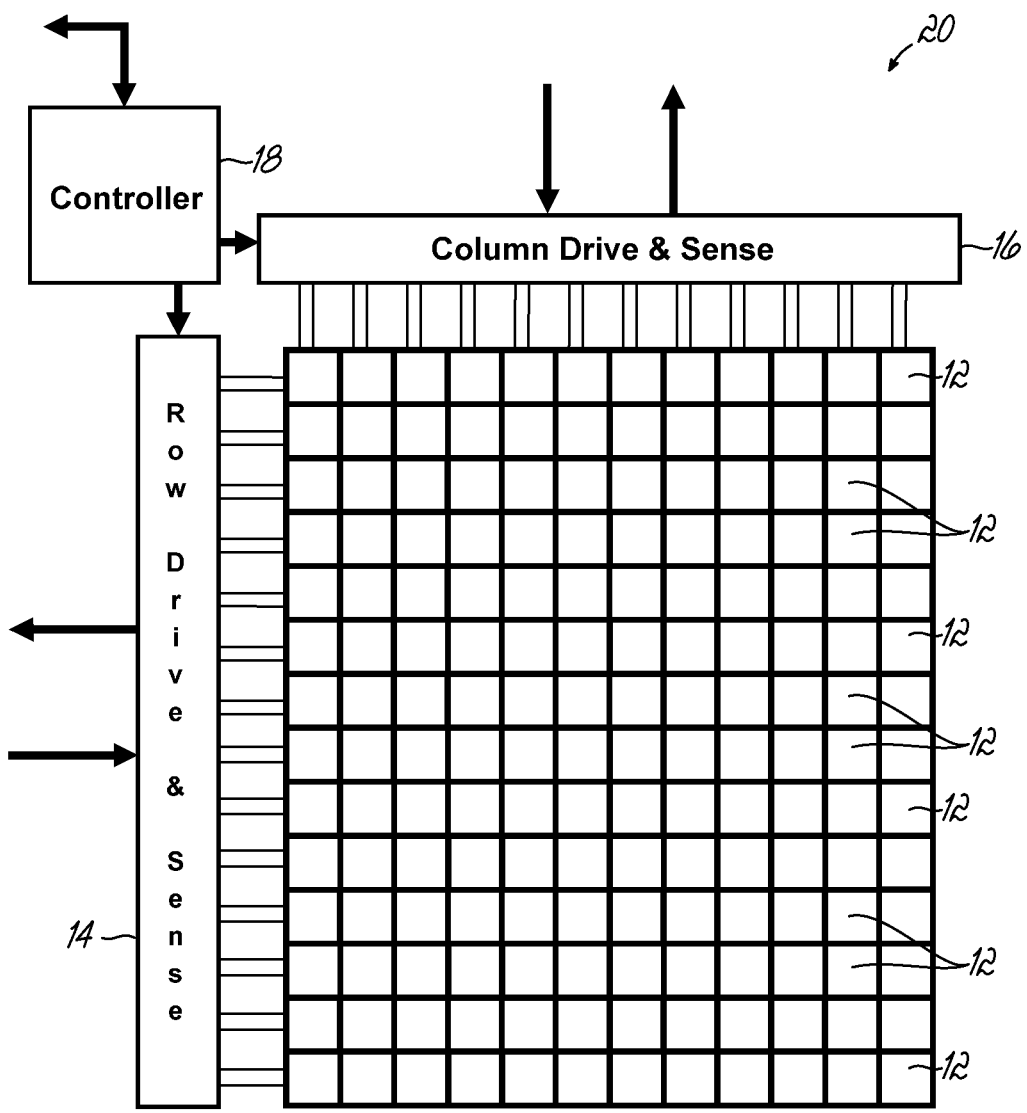
FIG. 2 illustrates a 196-cell sensor array with drive and sense electronics included for both the rows and columns of the cell matrix in accordance with an embodiment of the invention.

If a separate reference cell is required for each cell that will perform analyte analysis, then as many as 192 cells 12 may be required for a cell matrix to analyze 96 samples. An exemplary cell sensor array 20 is shown in FIG. 2. In this case, 144 cells are shown, by way of example, however, the array can be any size. The setup and operation of larger arrays is just like that of the 96-cell sensor array 10. The application of power (represented by inward arrows) and the output signal (represented by outward arrows) from the selected cells are also shown in FIG. 2. To that end, a similar cell matrix of any size may be constructed, such as one with 384 cells.

Microbridge Sensor Element Structures

Figure 3:
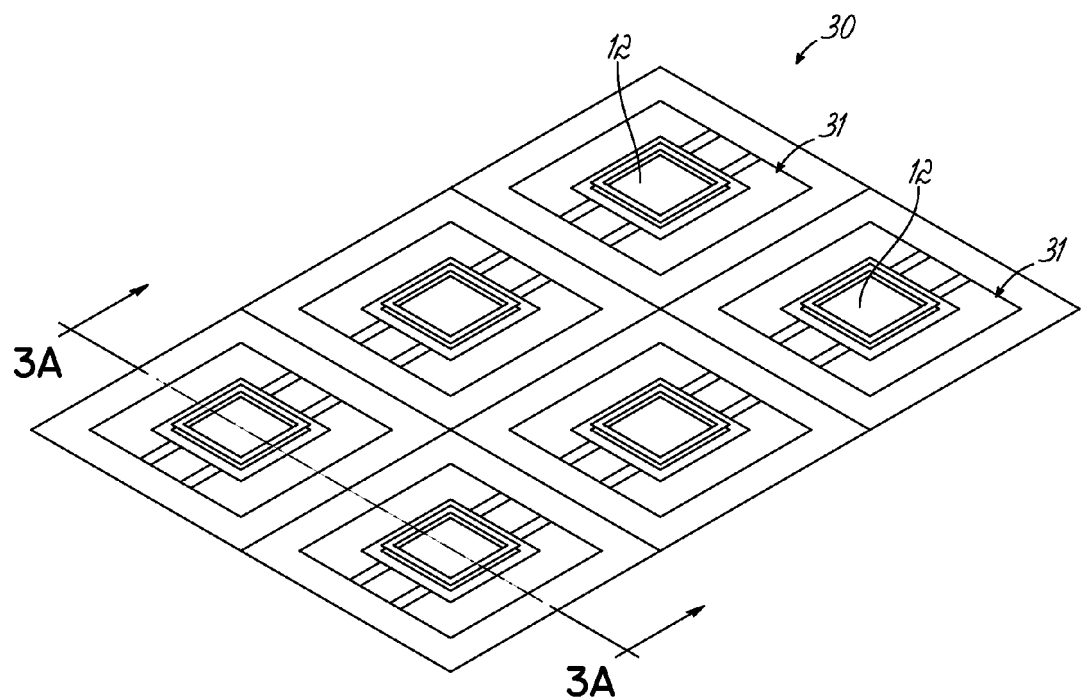
FIG. 3 is a perspective view of a sensor array with microbridge sensor elements in accordance with an embodiment of the invention.
Figure 3A:
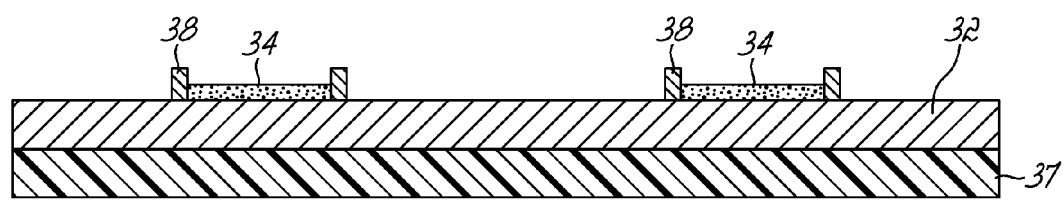
FIG. 3A is a cross-sectional view of FIG. 3 taken along section line 3A-3A.

FIGS. 3 and 3A show a sensor array 30 having microbridge structures 31 for the sensor cells 12 within the array. The sensor cells 12 together define a matrix of analysis sensor cells. Here, the microbridge structures 31 include a bridge support structure or platform 32 that is suspended, at least in part, over a space to allow precise heating control of the platform 32 and any analyte deposited in its corresponding cell 12, without heat being drained rapidly away from the platform 32 by surrounding structures. In one example, the platform 32 is composed of silicon and fabricated with micromachining techniques, as are well known in the art. Microbridge structures 31, as shown in FIG. 3, may be utilized individually for applications only requiring a single analyte, in clusters requiring a small number of sensor elements, or in a larger matrix of cells, such as those shown in FIGS. 1 and 2, for example.

As further shown in FIGS. 3 and 3A, each platform 32 includes a heating element 34, which may also include a temperature sensor element. In one embodiment, the heating element 34 and the temperature sensor element comprise a single or unitary resistive element 34, which is used both for heating and temperature sensing. The resistive element can be made from silicon, polysilicon, or a resistive metal such as platinum, Nichrome or tungsten, and the like. When a separate heating element and temperature sensor element are included on the platform 32, they may be oriented side-by-side in the same plane, interspersed in the same plane, or constructed on different layers of a multilayer/multi-plane structure, as further described and shown below. The shape of the heating element 34 may vary with different patterns providing different heat dispersion and conduction characteristics when an analyte substance is present on the platform 32. As further shown in FIG. 3A, the sensor array 30 also includes a substrate 37, which can be composed of silicon in a preferred embodiment, and the platform 32 may further include liquid retention walls 38 that may be optionally constructed on the platform 32 to assist in containing drops of liquid analyte when placed on the cell 12. The liquid retention walls 38 can be constructed from any compatible material such as polysilicon, silicon dioxide, silicon nitride, or a metal film, and the like. The array 30 is operated by applying power to the heating element 34 and sensing the temperature with the sensing element 34, as previously described. In a preferred embodiment, the heating element and sensing element are the same implanted resistor in the silicon platform 32, fabricated with standard integrated circuit processing techniques.

Figure 4:
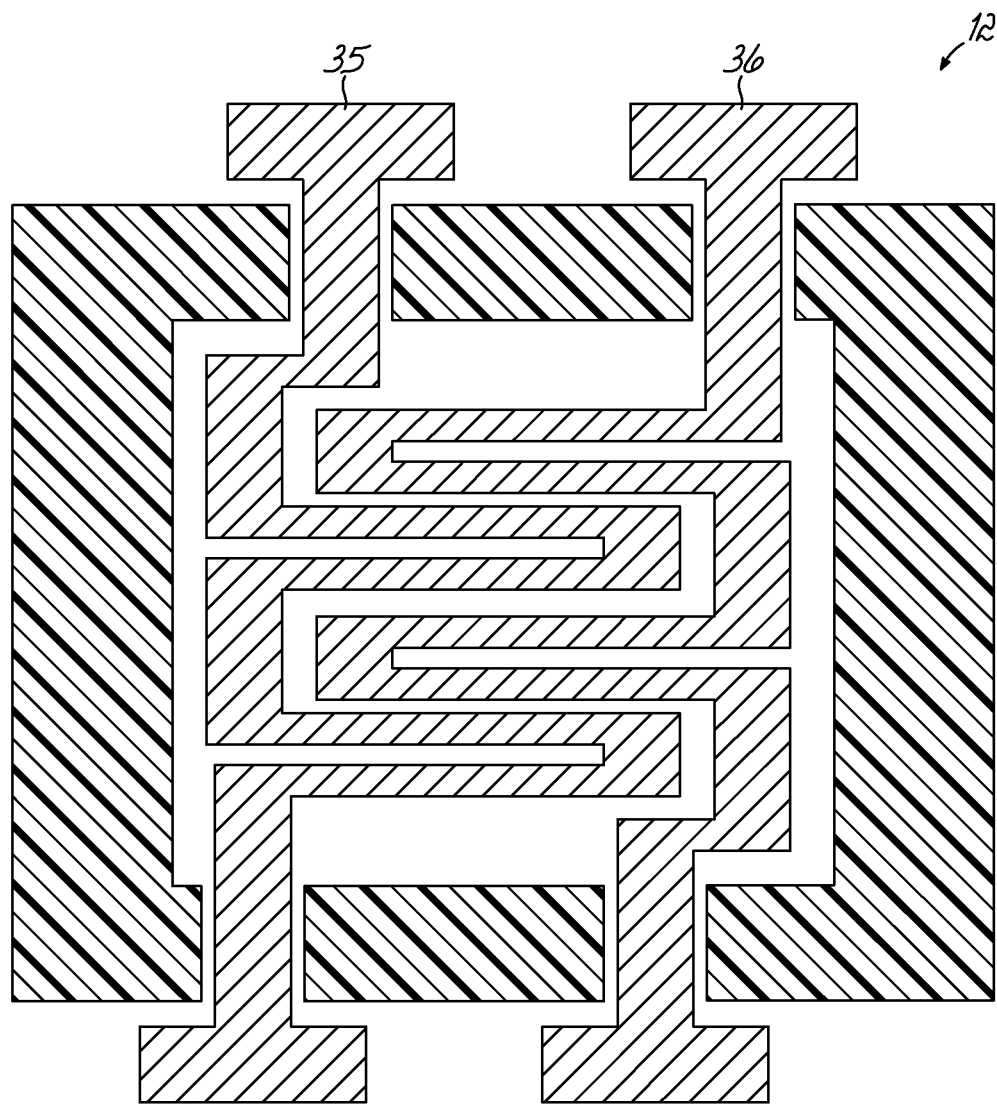
FIG. 4 shows an analysis cell of the microbridge structure of FIG. 3 with two resistive elements interleaved in a serpentine fashion.

FIG. 4 shows a single microbridge analysis cell 12, like that of FIGS. 3 and 3A, where two separate resistive elements 35 and 36 are interleaved in a serpentine fashion. In one embodiment, these resistive elements 35, 36 are both thin film resistors deposited on a dielectric layer (not shown), by means and methods known in the art. In another embodiment, these resistive elements 35, 36 are formed by etching doped conductive silicon to separate the two serpentines electrically. In yet another embodiment, these resistive elements 35, 36 are created by implanting resistors, and contacts are created at the end points for connection to the row and column buses shown in FIGS. 16 and 17, for example. Of the two serpentine resistive elements 35, 36 shown in FIG. 4, in one embodiment, one can be used for heating and the other can be used for temperature sensing. In another embodiment, both resistive elements 35, 36 can be used for heating and temperature sensing, as described elsewhere herein. The resistive elements 35, 36 may be electrically isolated from the sample by a dielectric layer, such as oxide or nitride, unless it is desired for the sample to be electrically active, as described further below.

Figure 5:
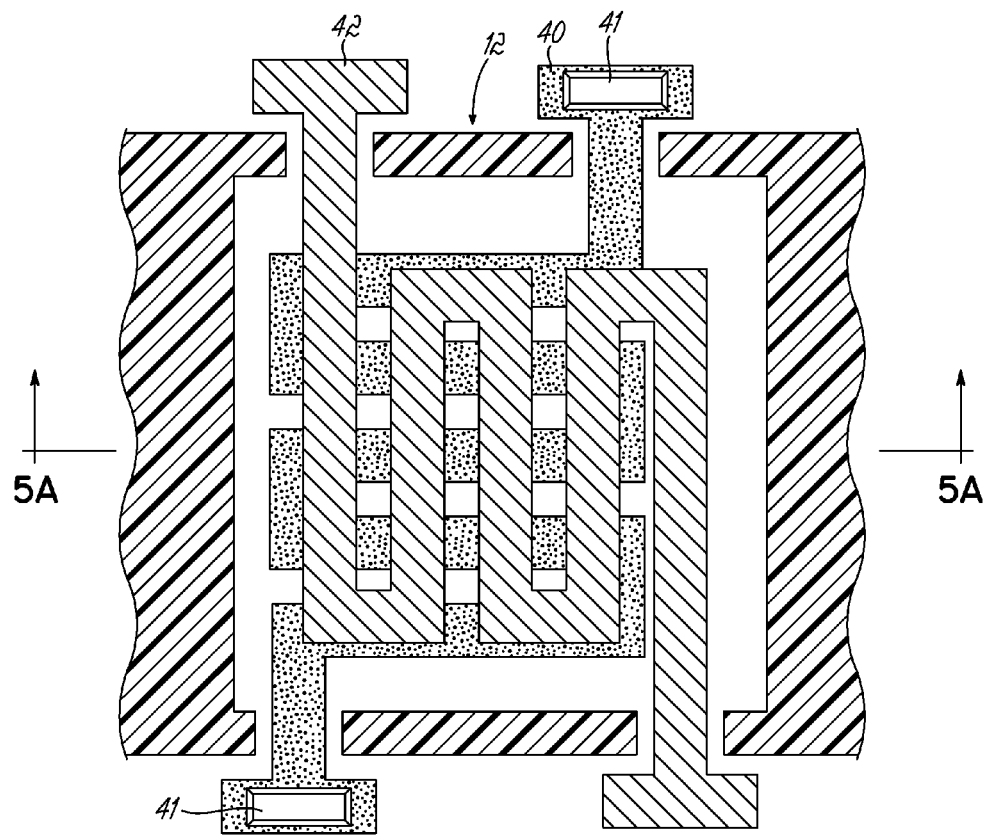
FIG. 5 shows an alternative embodiment of the analysis cell of the microbridge structure of FIG. 3 with two resistive elements.
Figure 5A:
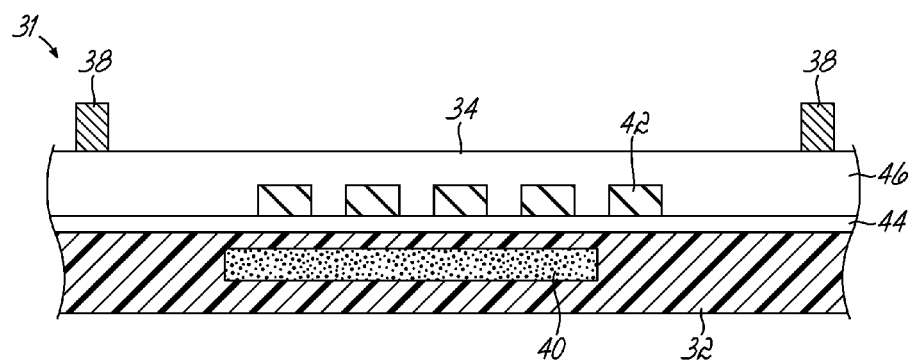
FIG. 5A is a cross-sectional view of FIG. 5 taken along section line 5A-5A.
Figure 16:
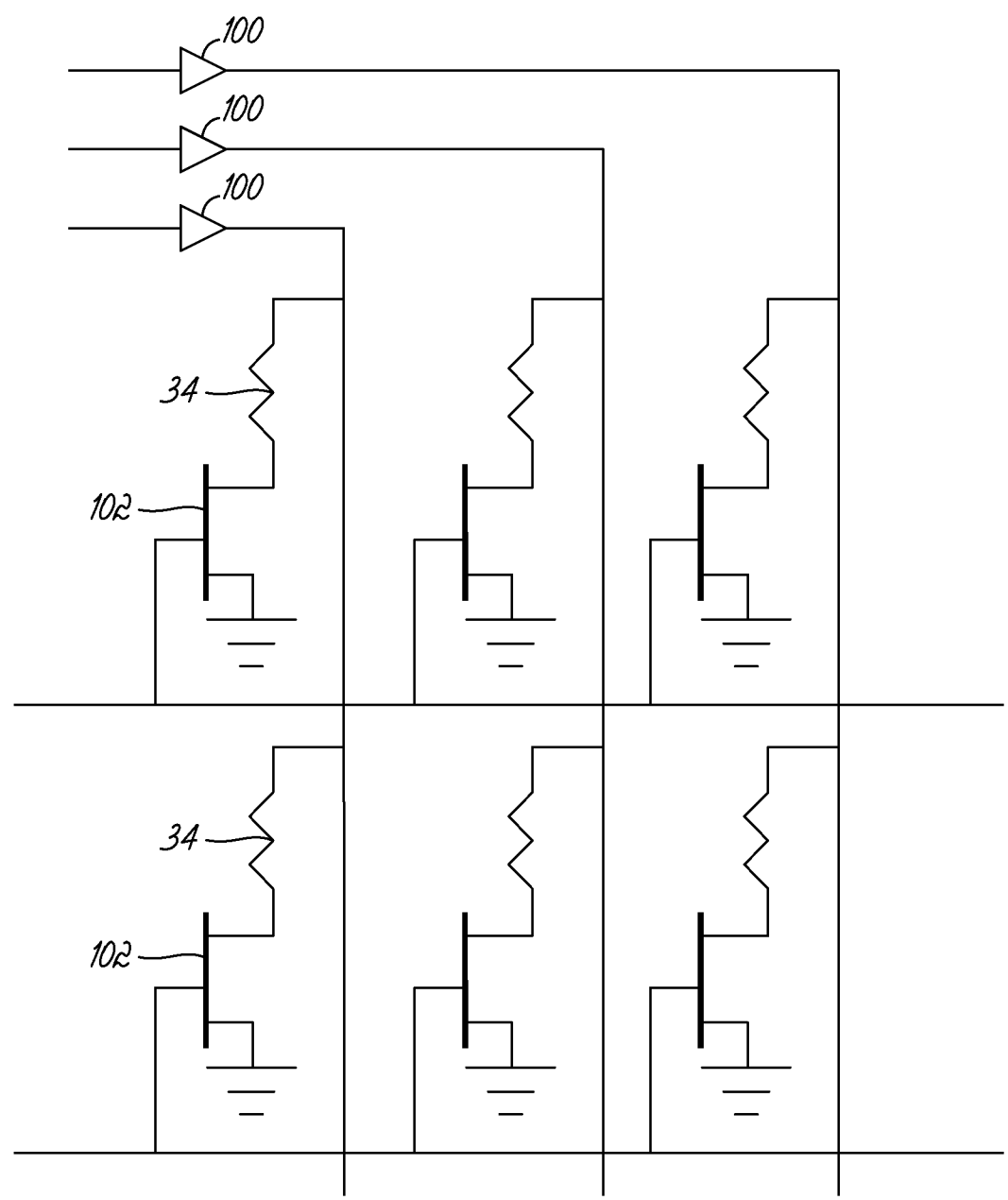
FIG. 16 is a schematic diagram of an embodiment for driving an array of cells where each cell contains a resistive element that is used for both heating and temperature sensing.

FIGS. 5 and 5A show another embodiment of the microbridge analysis cell 12, with microbridge structure 31, using separate resistive elements or resistors 40 and 42. Here, a first serpentine-shaped resistor 40 is formed using an implanted resistor structure with contacts 41 created at the end points for connection to the row and column buses, as shown in FIG. 16, while a second serpentine-shaped resistor 42 is formed above the first serpentine-shaped resistor 40 using a thin film resistor structure. In addition, the second serpentine-shaped resistor 42 is deposited on dielectric layer 44. Additionally, liquid retention walls 38 optionally may be added above the second serpentine shape resistor 42, as shown, to retain liquid or solid analytes. In FIG. 5A, the walls 38 are shown on top of dielectric layer 46 that electrically isolates the resistor 42 from the sample well formed inside the walls 38. In the preferred embodiment, the dielectric layers 44, 46 should be as thin as possible to promote efficient heat transfer between the resistor(s) 40, 42 and the sample. In one embodiment of the invention, the first resistor 40 is used for heating, while the second resistor 42 is used for temperature sensing. In yet another embodiment, both resistors 40, 42 may be used simultaneously for both heating and temperature sensing.

Figure 6:
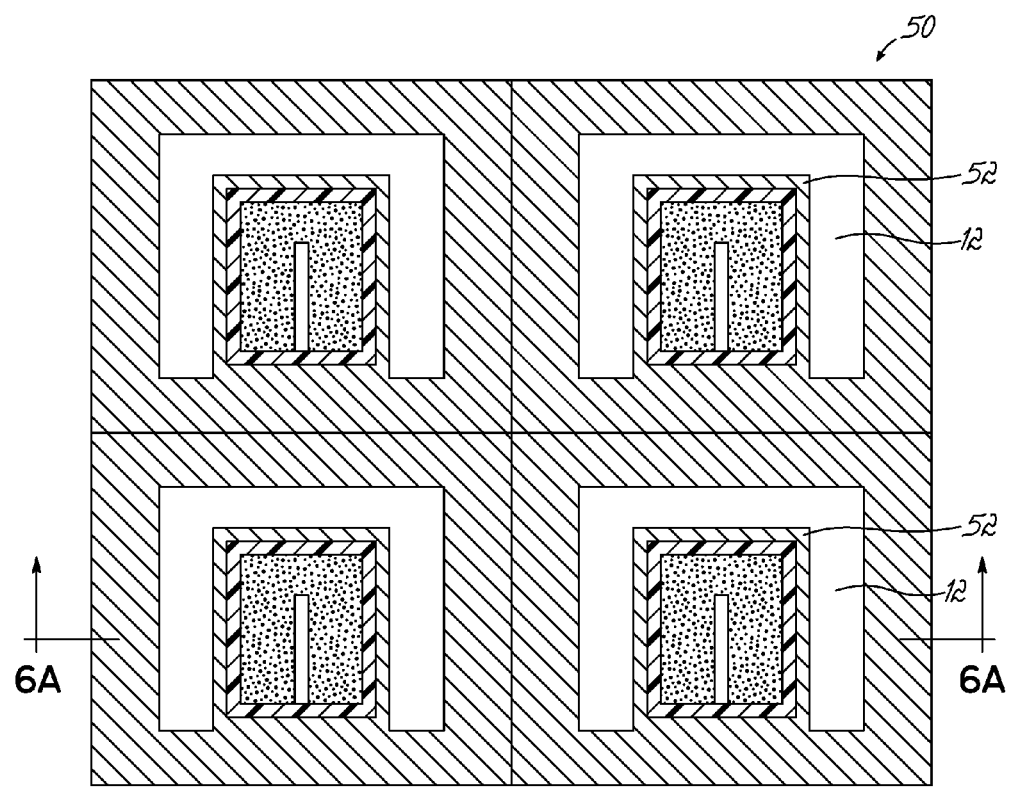
FIG. 6 shows a sensor array with analysis cells having a "diving board" style cantilever in accordance with an embodiment of the invention.
Figure 6A:
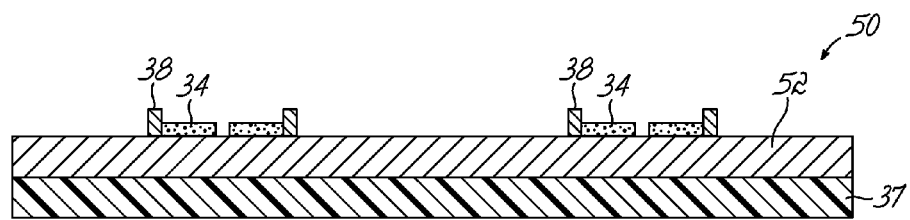
FIG. 6A is a cross-sectional view of FIG. 6 taken along section line 6A-6A.

FIGS. 6 and 6A show another embodiment of a sensor array 50 with analysis sensor cells 12 having a "diving board" style cantilever 52. As shown, the cantilevers 52 can be supported at one end or, alternatively, the cantilevers 52 can be supported at both ends (not shown). If the cantilevers 52 are supported at both ends, the electrical connections to the heaters and temperature sensors 34 can be made at either end. The analysis cell 12 can be utilized as a single sensor element or in multi-cell array 50. Similar to the sensor array 30 of FIG. 3, liquid retention walls 38 may optionally be constructed to assist in retaining liquid or solid analytes. Here, the walls 38 are constructed on the cantilever 52. Again, heating element 34 is shown included as part of the cantilever 52, which can also function as a temperature sensing element. In a preferred embodiment, an implanted resistor embedded in the cantilever provides both the heating and temperature sensing element. Alternatively, a temperature sensor element can be included separately on each cantilever 52. Again, when a separate heating element and temperature sensing element are included on the cantilever 52, they may be oriented side-by-side in the same plane, interspersed in the same plane, or constructed on different layers of a multilayer/multi-plane structure. And, the shape of the heating element 34 may vary with different patterns providing different heat dispersion and conduction characteristics when an analyte substance is present on the cantilever 52. As shown in FIG. 6A, the sensor array 50 also includes substrate 37, and the heating element 34 in one exemplary and non-limiting embodiment is depicted as a "U" shape.

Figure 7:
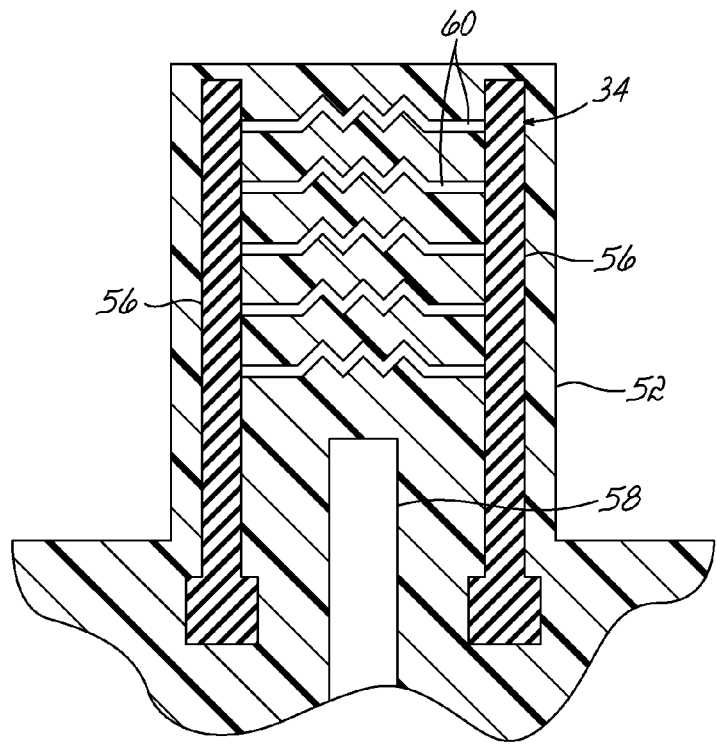
FIG. 7 shows a cantilever of the array of FIG. 6 for heating and/or temperature sensing of an analyte in accordance with an embodiment of the invention.
Figure 8:
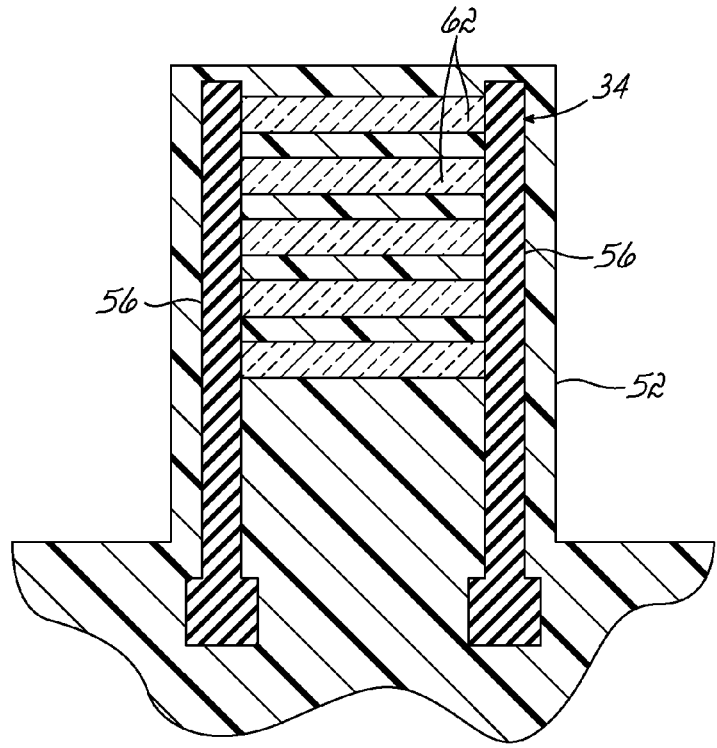
FIG. 8 shows another embodiment of a cantilever for heating and/or temperature sensing of an analyte in accordance with the invention.

FIGS. 7 and 8 show alternative embodiments of cantilever 52 with heating element 34 and/or temperature sensor element, which may be one in the same, with particular attention being paid to how resistance paths are formed therein. In FIG. 7, heavily doped regions, for example, silicon doped with concentrations of approximately $10^{18}$ or greater in the cantilever 52 form low resistance rails 56 running along the edges of the cantilever 52, with the remainder of the surface of the cantilever 52 covered with a lighter or nominally doped silicon, for example, silicon doped with concentrations of approximately $10^{18}$ atoms per cubic centimeter or less. These dopants can be n-type or p-type as is commonly known in the art. N-type dopants include phosphorus and arsenic and p-type doping is typically done with boron. A slot 58, for example, is also constructed through the cantilever 52 thereby separating conductive paths 60 in the vicinity of the base of the cantilever 52. Between the two heavily doped and more conductive rails 56, the effective resistance of the lighter doped silicon is represented in FIG. 7 as a number of separate resistors or conductive paths 60, although in reality the resistance is continuous between the two conductive rails 56.

In FIG. 8, two conductive rails 56 are shown along the edges of the cantilever 52 similar to the structure of FIG. 7, with these rails 56 being constructed using heavily doped silicon having greater conductivity. Connected between these rails 56, segments 62 of lighter doped silicon are shown, with spaces of un-doped silicon between them. Although not shown in FIG. 8, the widths of these lightly doped segments 62 may vary along the length of the cantilever 52, as well as varying the spacing between the segments 62, in order to provide a pattern of conductive paths for optimum heating distribution of an analyte placed on the cantilever 52. In order to isolate the various doped rails 56 and segments 62 shown in FIG. 8, the doped rails 56 and segments 62 may be formed by constructing P-type resistors on an N-type silicon substrate, or alternatively constructing N-type resistors on a P-type silicon substrate, by means and methods known in the art. In this embodiment, the structure of FIG. 8 does not require slot 58 (see FIG. 7) etched through the cantilever 52 in order to separate conductive paths though the slot 58 provides the preferred embodiment.

Figure 9:
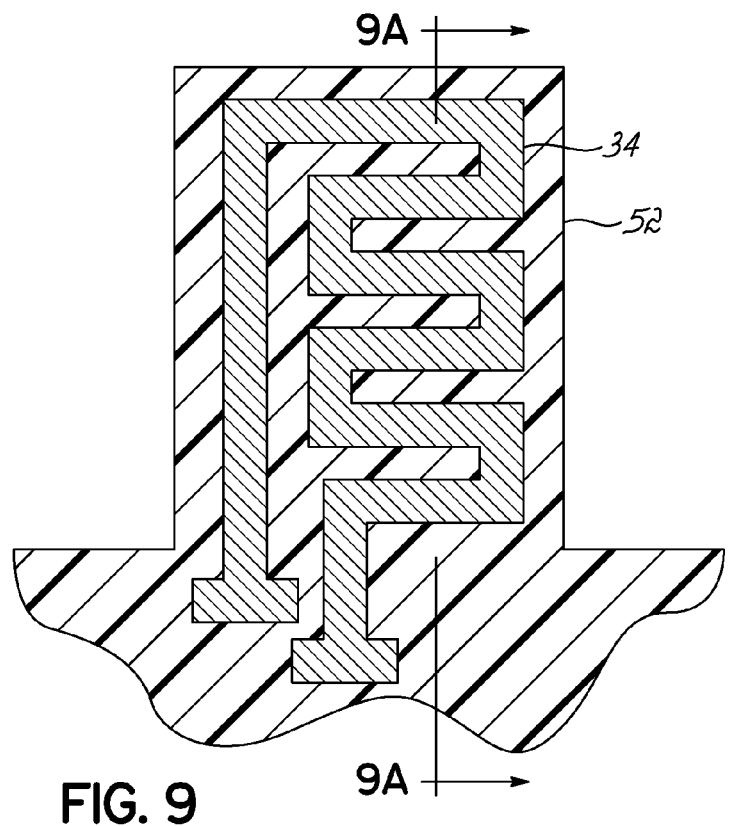
FIG. 9 shows another embodiment of a cantilever for heating and/or temperature sensing of an analyte in accordance with the invention.
Figure 9A:
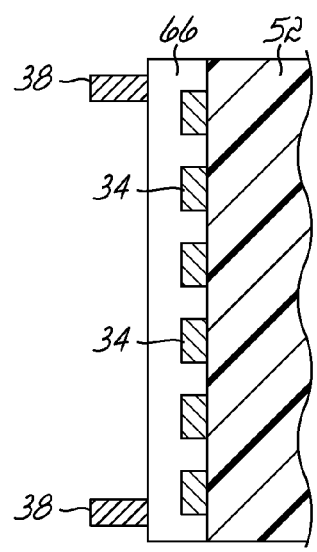
FIG. 9A is a cross-sectional view of FIG. 9 taken along section line 9A-9A.

FIGS. 9 and 9A show yet another embodiment for a resistive structure, such as a heating and/or temperature sensing element 34, which is included in cantilever 52. Here, a serpentine structure is formed using a thin-film resistor structure to form the heating and/or temperature sensing element 34. Metals are typically deposited as part of forming a thin-film resistor, with common choices being tungsten (W), titanium tungsten (TiW), nickel chromium (NiCr), and the like. As also shown, the element 34 may be included within a dielectric layer 66, which may further include liquid retention walls 38 thereon that may be optionally constructed to assist in containing drops of liquid analyte when placed on the cantilever 52.

Figure 10:
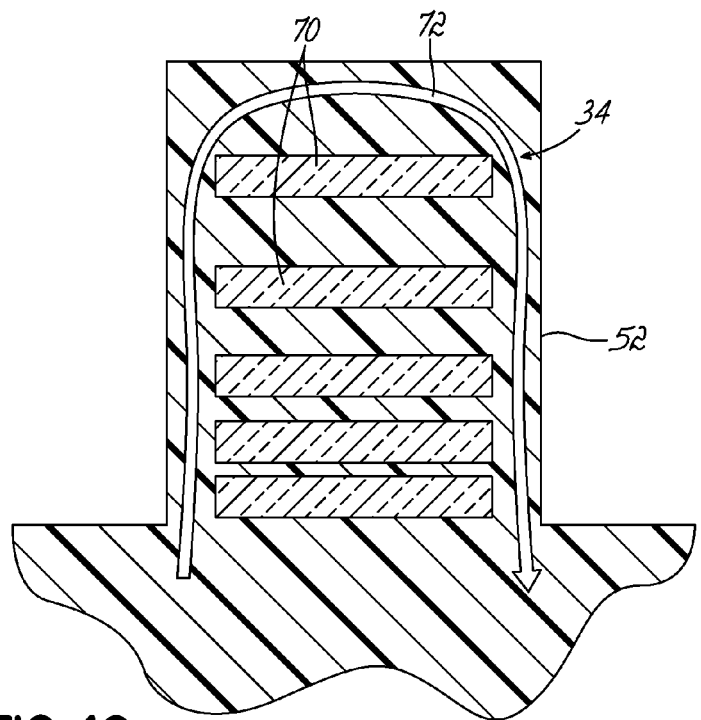
FIG. 10 shows another embodiment of a cantilever for heating and/or temperature sensing of an analyte in accordance with the invention.

FIG. 10 shows another embodiment of a resistive structure, such as heating and/or temperature sensor element 34, included in cantilever 52. In FIG. 10, slots 70 can be etched through silicon to separate conductive paths in the cantilever 52, which typically can be covered with a constant doping level. The slots 70 may be formed with a variable spacing to alter the distribution of resistance. Alternatively, or in combination, slots 70 may be formed with variable widths and thereby can also alter the distribution of resistance over the surface of the cantilever 52. With the locations of slots 70 as shown in FIG. 10, lowest resistance path 72 occurs around the periphery of the cantilever 52 and is focused toward the tip of the cantilever 52.

Figure 11:
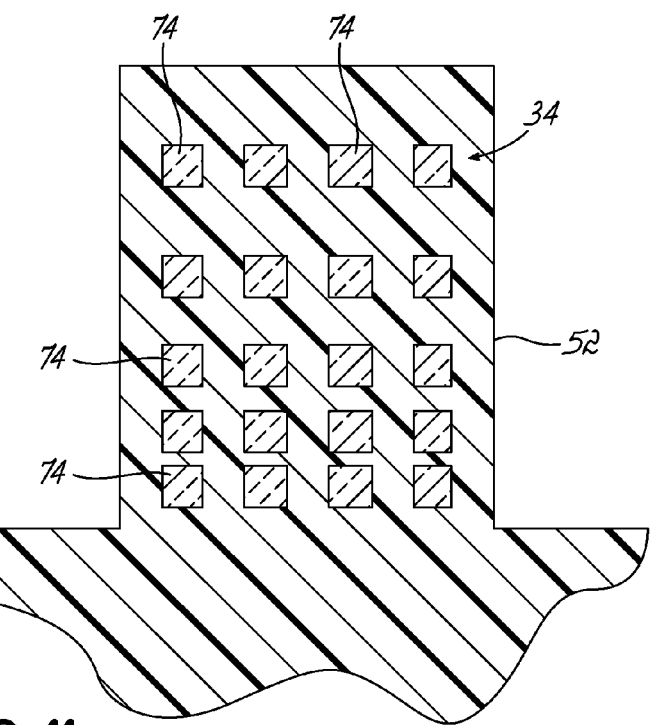
FIG. 11 shows another embodiment of a cantilever for heating and/or temperature sensing of an analyte in accordance with the invention.

FIG. 11 shows a similar structure to that of FIG. 10, except that instead of slots 70, rows of holes 74 are formed through the cantilever 52 to form a "waffle" pattern by means and methods known in the art. The holes 74 may be circular or square, for example, and some shapes of holes may be advantageous for construction according to the preferences of the manufacturing facility. Forming holes 74 or slots 70 through the cantilever 52 serves a number of purposes. Besides altering the resistance on the surface of the cantilever 52, these add surface area to the extent that the internal edges of the slots 70 or holes 74 are able to interact with an analyte. These holes 74 and slots 70 also lighten the cantilever 52, which in some applications may be useful. In FIG. 11, the spacing between the rows varies, which serves to alter the distribution of resistance/conductance across the width and length of the cantilever 52. In a preferred embodiment, the heating element 34 in FIGS. 4-11 is arranged to provide uniform heating across the sensor surface.

Further embodiments of cantilevers 52 with slots 70 or holes 74 formed therethrough includes constructing cantilevers 52 that are stacked one above the other. In one example, using a double device layer wafer (not shown) with an extra oxide layer, it is possible to create stacked cantilever, bridge, and serpentine bridge structures that can be heated and sensed with current driven through the structures. A pair of stacked cantilever structures can be fabricated with holes 74 at different locations such that an air or liquid sample will have to make a sharp turn as it flows through a top cantilever and then to and through a second cantilever directly below it. This convoluted path design helps increase analyte interaction with the cantilever surface for better thermal interaction with the liquid and better capture efficiency for analytes in vapor analysis applications.

Figure 12:
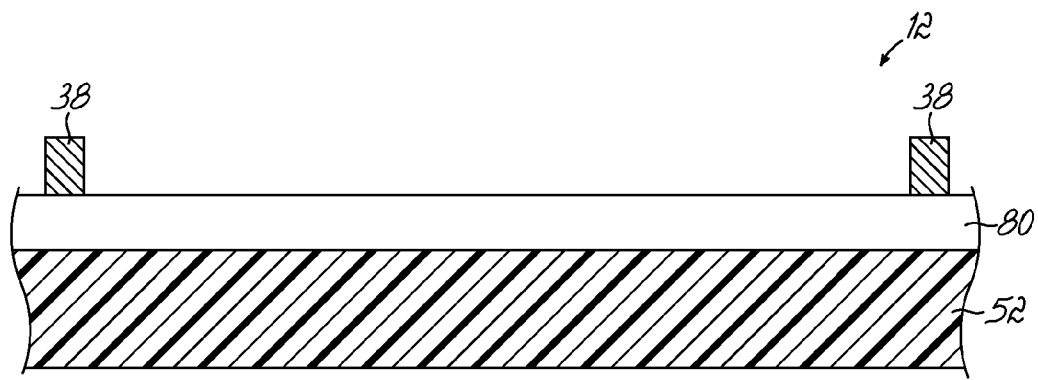
FIG. 12 shows a cross-sectional view of a cantilever with an analyte well in accordance with an embodiment of the invention.
Figure 13:
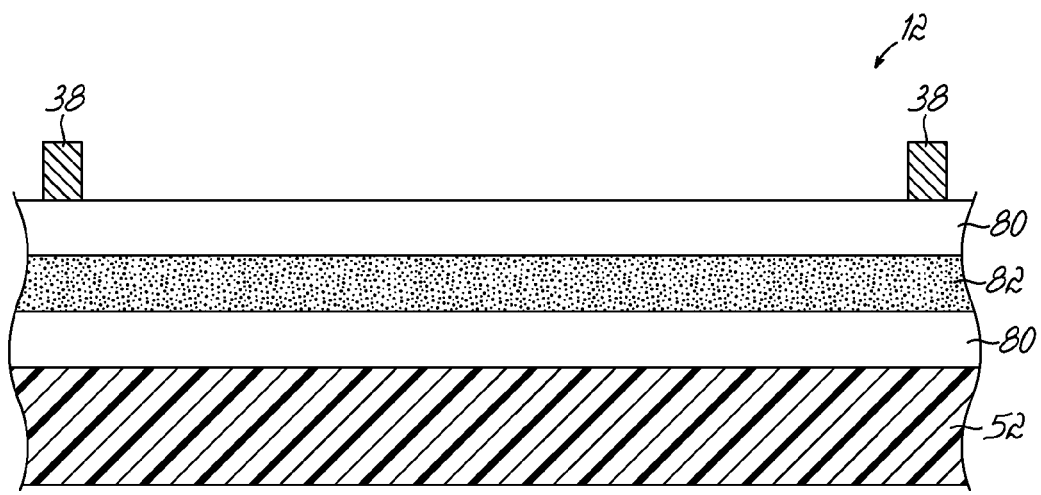
FIG. 13 shows a cross-sectional view of a cantilever with an analyte well in accordance with another embodiment of the invention.

FIGS. 12 and 13 show alternative embodiments of analyte wells or cells 12, which may be incorporated, for example, into either the cantilever 52 or the microbridge structure 31 (FIG. 3). In FIG. 12, a dielectric layer 80 is formed over the cantilever 52 with walls 38 formed above to retain liquid or solid analytes. FIG. 13 shows a heat spreader 82 formed between two dielectric layers 80. Resistant elements 34, such as for heating and/or temperature sensing are not shown here for simplicity, however, the presence of the heat spreader 82 aids in distributing heat for some applications. An effective material for constructing the heat spreader 82 includes, for example, a metallic material, such as aluminum, and the like.

Figure 14:
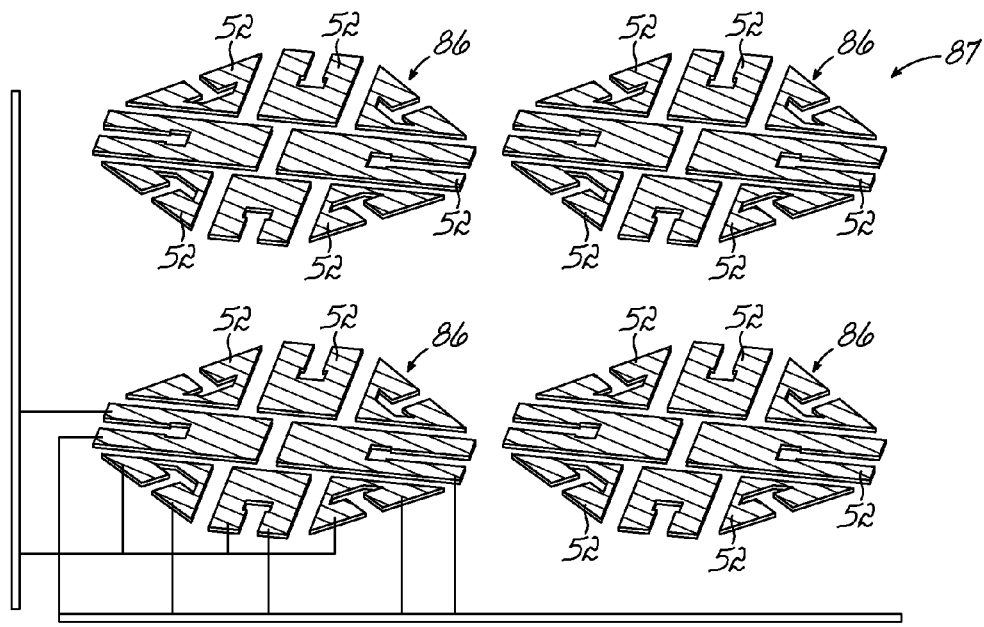
FIG. 14 is a perspective view of an embodiment of sensor arrays with cantilevers arranged in a radial orientation.

While a conventional array of microcantilevers would typically have cantilevers arranged in rows, other configurations are possible including the unique arrangement shown in FIG. 14 where cantilevers 52 are arranged in a radial orientation, and can be utilized in any of vapor, liquid, and/or solid analysis applications. Here, differently shaped cantilevers 52, i.e., 4 diving board cantilevers and 4 arrowhead shaped cantilevers, tile together closely thereby forming a single cluster 86 with relatively small gaps between cantilevers 52. The four clusters 86 shown in FIG. 14 together form a 2×2 sensor array 87. In this design, the cantilevers 52 are supported (not shown) at the perimeter of the cluster 86. This radially oriented cluster 86 serves multiple purposes. First, it maximizes the ratio of total cantilever surface area to the gap area between cantilevers 52. When used in a vapor sensing application, this maximizes the probability that molecules entering a sensor inlet will land on a surface of the cantilever 52 and not pass through a gap between the cantilevers 52. When used for liquid analysis applications, this structure maximizes the retention of liquids on the cantilevers 52 as surface tension will cause many liquids to bridge over the gaps and be retained on the cantilever 52 surfaces rather than slipping through the openings between the cantilevers 52. This also allows analyte material, and materials evolved from analytes during analysis, to be flushed through the cluster 86 after an analysis cycle is completed. A flushing operation can be accomplished utilizing a pump and vacuum mechanism, which causes the cantilevers 52 to bend under the pressure allowing the elimination of the sample.

The multi-cell structure of FIG. 14 can be constructed on a single chip by means and methods known in the art and utilizes a radially oriented cantilever cluster 86 that includes two distinctly separate shapes of cantilever 52 to effectively tile them together with minimal gaps. In one embodiment of a multi-cell array design, multiples of cantilevers 52 in a single cluster 86 are driven and sensed simultaneously when wired, as shown for the lower left cluster 86 of FIG. 14, and connected to drive and sense circuits as described in this application. In a preferred embodiment, all of the cantilevers 52 are used for thermal analysis. For example, a liquid sample may cover a significant portion of the cluster 86. The controlling circuitry, as described in this application, can apply power to the cantilevers 52 to heat the sample and perform a thermal analysis, such as DSC or DTA.

In another preferred embodiment, operation of the cluster 86 of cantilevers 52 can be performed as described in U.S. Pat. No. 8,524,501, the contents of which is expressly incorporated by reference herein in its entirety. As described therein, some of the cantilevers 52 in the cluster 86 can include a piezoelectric film (not shown) that allows the cantilevers 52 to be resonated and the frequency sensed so that the mass on the cantilever 52 can be measured. In another preferred embodiment, mass sensing analysis can be combined with thermal analysis. In this embodiment, some of the cantilevers 52 can include a piezoelectric film for mass sensing and some do not include the piezoelectric film but rather, include the heating structures described herein. The combined mass measurement data and thermal analysis data provides a more comprehensive analysis of the sample. In this analysis, at least a portion of the cantilevers in each cluster includes a chemically sensitive active area. Analysis of a sample can be performed by measuring the mass of the sample adsorbed or absorbed onto each of the resonating cantilevers and performing thermal analysis of the sample with non-resonating cantilevers. Alternatively, with more elaborate electronics to drive the cluster 86, each cantilever 52 in a cluster 86 can be actuated and sensed individually. In this embodiment, the individual resistors are wired out to the drive and sense circuitry to allow each heater and temperature sensor to be actuated individually with individual circuits or with a multiplexing circuit. Such implementations are routine for skilled electronics designers. Activating individual cantilevers 52 or a subset of cantilevers 52 in the cluster 86 may be useful to perform one test on a portion of the analyte retained on the cluster 86, followed by another test performed on a different portion of the analyte on the cluster 86. As with other sensor element configurations described herein, a cluster style structure can be utilized for analysis of vapor, liquid, and/or solid analytes.

Figure 15:
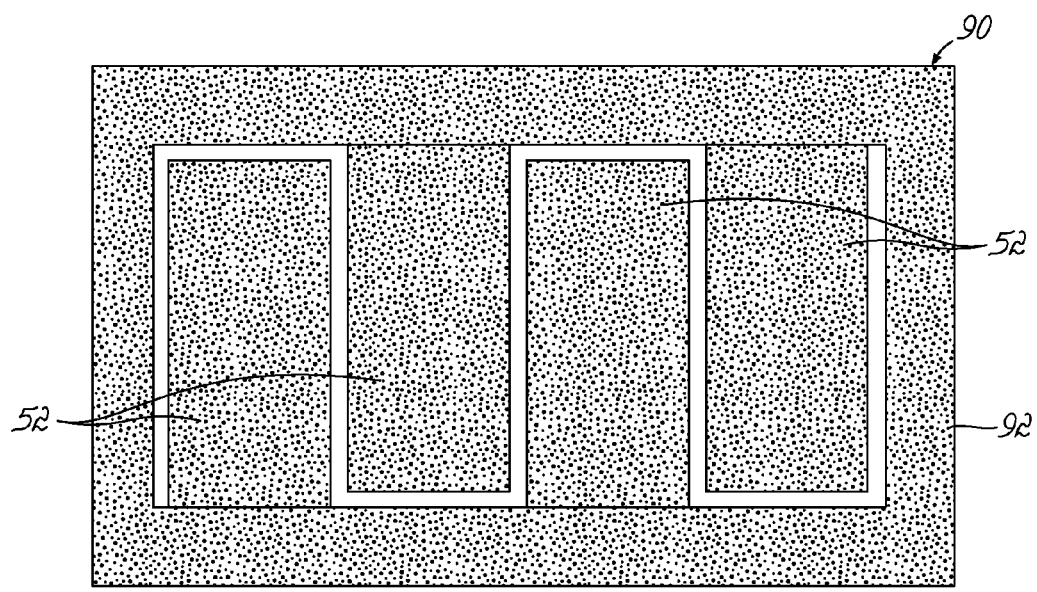
FIG. 15 shows an embodiment of a sensor array with cantilevers arranged in a baleen orientation.

FIG. 15 shows another embodiment of a cluster 90, in this case a rectangular cluster 90 of cantilevers 52, which provides some of the same benefits as the radially oriented cluster 86 of FIG. 14. Here in FIG. 15, cantilevers 52 are interspersed in a form of a "baleen" structure, with minimal gaps between adjacent cantilevers 52, and minimal gaps between the cantilever 52 and adjacent sensor chip structure 92. The resulting overall gap typically forms a serpentine structure as shown in FIG. 15. This structure, maximizes the ratio of analyte that is captured on the cantilever 52 versus the analyte lost through a gap, and at the same time provides for the ability to flush any remaining analyte through the gaps when liquids are analyzed. As with FIG. 14, the cantilevers 52 shown in FIG. 15 may be driven and sensed individually or simultaneously, and if simultaneously, may be "ganged" together to act in unison, like that of the cluster 86 of FIG. 14.

When cantilever clusters 86, 90 are utilized, multiple cantilevers 52 in the clusters 86, 90 may be driven by a single driver or alternatively may be driven and sensed individually. If driven and sensed individually, the outputs of multiple cantilevers 52 performing a similar test on a single sample of analyte may be summed to produce a resultant response with advantages. For example, summing the signals from four identical DTA cantilever sensors, in this case, the arrowhead shaped cantilevers 52 in the radially oriented cluster 86, were found to produce signal sizes more than twice that produced by one sensor alone. At the same time, the noise floor was kept nearly the same, effectively boosting the signal-to-noise ratio. This technique can also improve the number of measurements, N, and therefore improve reliability and repeatability. The technique could be used with an algorithm that does not incorporate outlier data from any one of the N measurements into the average. By boosting the sensitivity this way, slower ramping rates can be employed in thermal analysis, enabling greater selectivity, for even lower amounts of analyte.

Figure 17:
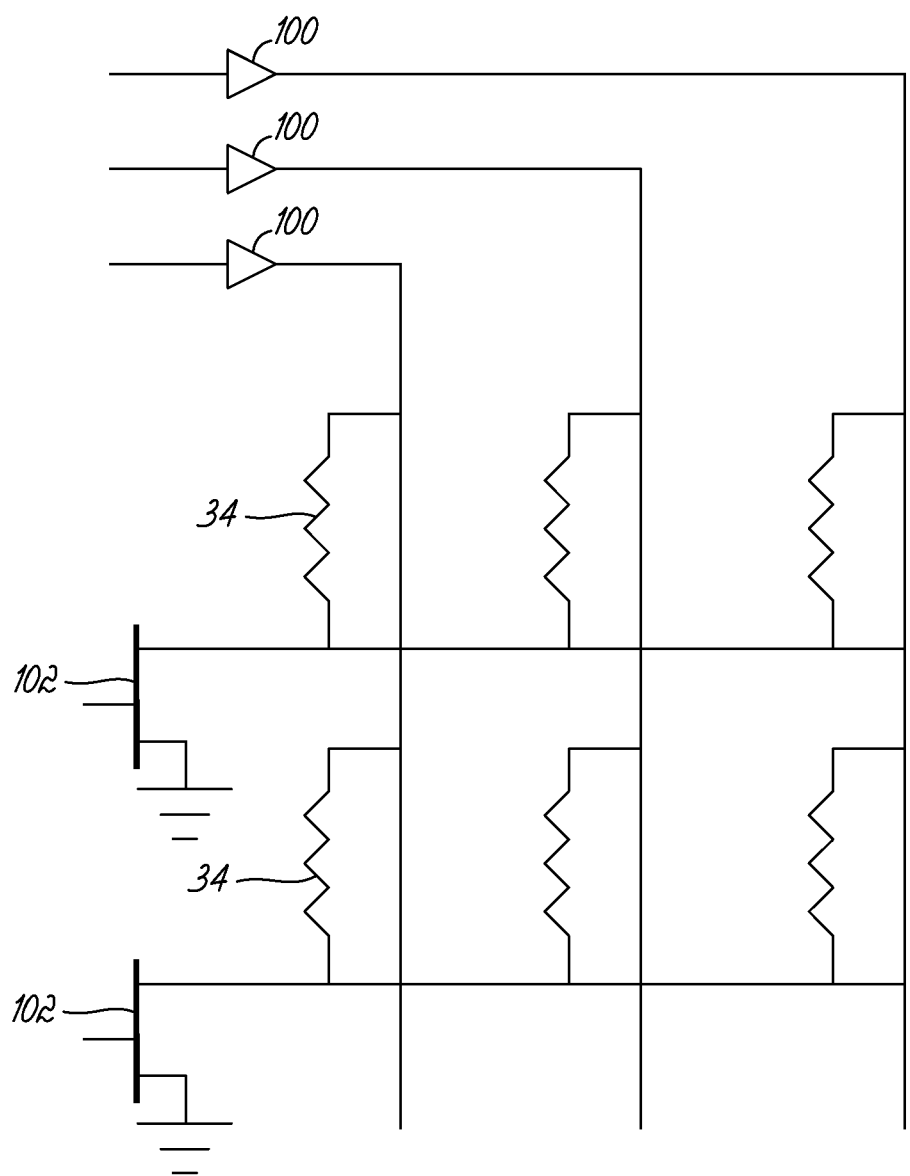
FIG. 17 is a schematic diagram of another embodiment for driving an array of cells where each cell contains a resistive element that is used for both heating and temperature sensing.

FIGS. 16 and 17 show alternative embodiments for driving an array of cells interfaced with drive and sense electronics where each cell contains a resistive element 34, which is used for both heating and temperature sensing. In both FIGS. 16 and 17, high current drivers 100 are used to drive the columns while the path to ground is completed through an analog switch 102 shown here, for example, as an N-FET. In FIG. 16, individual N-FETs are included for each resistive heating element 34, while in FIG. 17, a single N-FET 102 is utilized per row of heating elements 34.

FIG. 18 shows a more detailed view of an embodiment of a circuit for driving and sensing an array of cells where thermal analysis is performed by heating and temperature sensing using a common sensor element, which is marked MPS. At the top of FIG. 18, a precision current generator is controlled by a 20-bit D/A converter and steered through an analog mux to drive the heating elements. In a manner similar to FIG. 17, a single analog switch is used to complete the current path for all sensor elements in a row. The circuits of FIG. 18 refer to an 8-column, 16-row configuration (array of 128) but could also be used for an 8-column, 12-row configuration (array of 96), for example. With straightforward expansion or reduction in the size and complexity of these circuits, arrays of many different matrix configurations can be supported, and, as such, these figures should be considered exemplary and non-limiting.

Since the top of all resistive sensor elements in a column is connected together, one connection is made from this common point to an analog mux as part of temperature sensing. All of the sensor elements in a row have their connection to an analog mux made in common, and a point on this common connection is selected to become the other sensing terminal as part of a 4-wire or "Kelvin" measurement scheme. The output of this analog mux entitled DCol is connected to a differential amplifier in FIG. 19. For all sensing structures described herein, a "Kelvin" measurement scheme is the preferred architectural choice for sensing connections.

FIG. 19 shows multiplexers used for controlling both drive selection and sensing selection. Sensing points are labeled Com_R(n), where n equals 0 through 15, and represent the ground side sensing point connection for each MPS sensor element. These are selected in a 16:1 mux to feed one side of the differential amplifier in FIG. 19. Row selection signals control this multiplexer as well as the other analog mux shown in FIG. 19, which selects the analog switches in FIG. 18 to enable driving and sensing of a row. The output of the differential amplifier shown at the top of FIG. 19 connects to the high-resolution 24-bit ADC in FIG. 20. FIG. 20 also shows a controller embodiment that receives instructions from a processor via an SPI bus and selects the appropriate cell(s) 12 in an array as a result. Choices for DAC and ADC resolutions are typically chosen according to the accuracy requirements of a particular application.

According to this invention, differential analysis using thermal techniques can be performed by way of a number of alternative embodiments. For thermal analysis where ovens and thermocouples are used, it is traditional to have a pair of similar crucibles and temperature sensing mechanisms in order to analyze both an analyte and a reference simultaneously, the results then being compared to produce a differential result. The present invention offers alternative embodiments where results to be compared differentially are acquired sequentially for both DTA and DSC.

One embodiment of an analysis system according to the present invention, and compared with known DTA and DSC methodologies, utilizes the same sensor probe for both a primary measurement and a reference measurement while separating the measurements in time, hence, a "temporally separated DTA or DSC" analysis method, and eliminates the need to physically isolate the reference probe. This saves on complexity, size, and cost, while at the same time requiring fewer elements in a sensor array. Additionally, since fewer elements are required, it is then feasible to utilize multiple elements and perform redundant measurements, if advantageous for a particular application. The results of redundant measurements can then be averaged to produce more accurate and consistent results. Utilizing the same sensor probe for both primary and reference measurements has the additional benefit of removing from consideration subtle physical differences between primary measurement and reference sensor elements, since they are in fact the same element.

Figure 25:
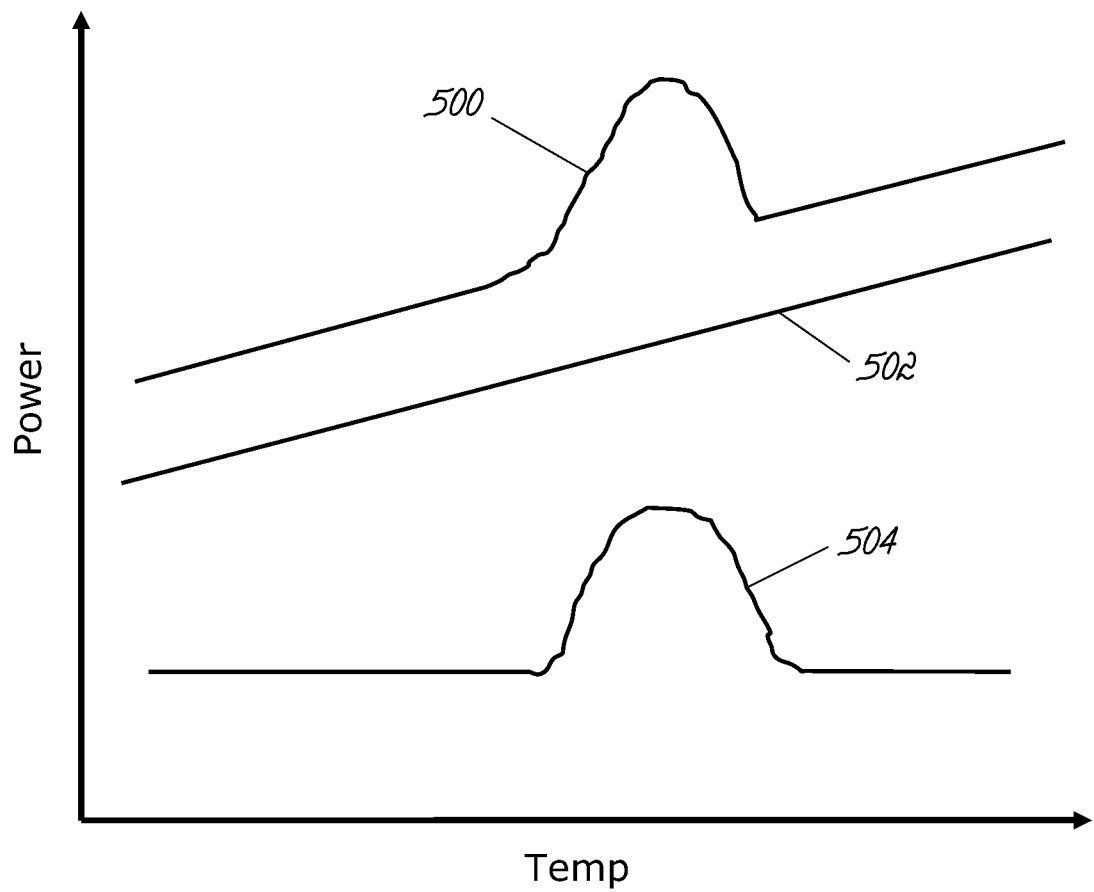
FIG. 25 is a graph showing result curves for sequential analysis performing DSC where power transferred to reference or analyte samples are graphed against temperature.

With reference to FIG. 21 and in accordance with embodiments of the invention, a flowchart for a temporally separated differential analysis method is shown that can be utilized for DTA or DSC analysis, or any other differential analysis process. At step 200, a temperature ramp cycle can be run on an analyte sample contained, for example, in an analysis cell, which includes a sensor element, e.g., heating and/or temperature sensor element 34. Next, a temperature ramp heat cycle is run at step 202 to clean the sensor element 34. The temperature ramp cycle can include heating the heating element 34 up to a desired temperature over a specified period of time. In one example, the time and temperature can be chosen to vaporize any material that may have accumulated on the sensing element 34. Where the initial analysis ramp on an analyte sample results in sufficient heat being applied to the sensor element to clean it sufficiently, the second step 202 may be one and the same with a third step 204 where a temperature ramp analysis cycle is run on a clean element 34 to capture reference data. For each temperature ramp, the data collected is the sensor temperature as a function of time for a DTA analysis or sensor power as a function of time for a DSC analysis, as shown in FIGS. 23 and 25, respectively. The data is collected, stored, and analyzed such as by a common computer system. The reference analysis data is subtracted at step 206 from analyte analysis data to produce a differential data result.

A variation on the analysis method of FIG. 21 is shown in FIG. 22, in which the reference analysis cycle includes analyzing a buffer liquid containing no analyte. As shown in FIG. 22, in the first step 300, an analysis cell or well containing a liquid buffer solution can be analyzed with a temperature ramp cycle in order to capture reference data. In an optional second step 302, any buffer solution remaining in the sensor well is extracted. Extraction can be performed by a suction mechanism with a probe inserted into the well. Alternatively, where a cluster of microcantilevers is utilized, forming an aggregate sensor element, extraction can occur by flushing the remaining buffer solution through the gaps between cantilevers. An optional heating cycle may also be performed at this point in step 302 to further clean the sensor element after any remaining buffer solution has been extracted.

Alternatively, if the presence of additional buffer solution is not detrimental to an analysis cycle on a solution containing analyte, the second step 302 may be skipped. In the third step 304, analyte solution is added to the same sensor well and a temperature ramp cycle is run on the analyte solution. In a final step 306, reference data is subtracted from the analyte analysis data in order to create data for a differential result.

For some forms of liquid analysis, for example, especially in biological applications, it may be desirable to perform multiple measurements on one analyte sample where between measurements an additional liquid is added to the cell where the analyte sample is located. This "titration" method is typically referred to as Isothermal Titration calorimetry or ITC and the technique is understood to be well known in the art. In general, ITC is a quantitative technique that can directly measure the binding affinity, enthalpy changes, and binding stoichiometry of the interaction between two or more molecules in solution. Typically, a solution containing a biomolecule ("solution A") is placed in a cell and a solution containing a ligand is injected into the cell multiple times. The system is programmed to maintain a constant temperature in the cell either increasing the power supplied to the cell to cause heating in the case of an endothermic reaction, or decreasing the power into the cell in the case of an exothermic reaction. Throughout the experiment and with each injection, the power required to maintain a constant temperature is recorded and compared to a reference cell that does not receive the injections of the ligand solution. If needed, reference data can be from an adjacent cell filled with Solution A or from a prior or subsequent test in the same cell that contains only Solution A and no ligand injections. Finally, reference data from the buffer solution A reference cycle is subtracted from the ligand injection data in order to create a differential data result. This ITC analysis method can be performed with very low volumes using the cell sensor arrays, as described herein, combined with small volume injections of ligand solutions made possible using, for example, commercially available ink jet and acoustic fluid transfer technologies, as known in the art. Such Ink jet technologies can transfer pL volumes, while acoustic technology can transfer down to 25 nL at the current time.

Figure 24:
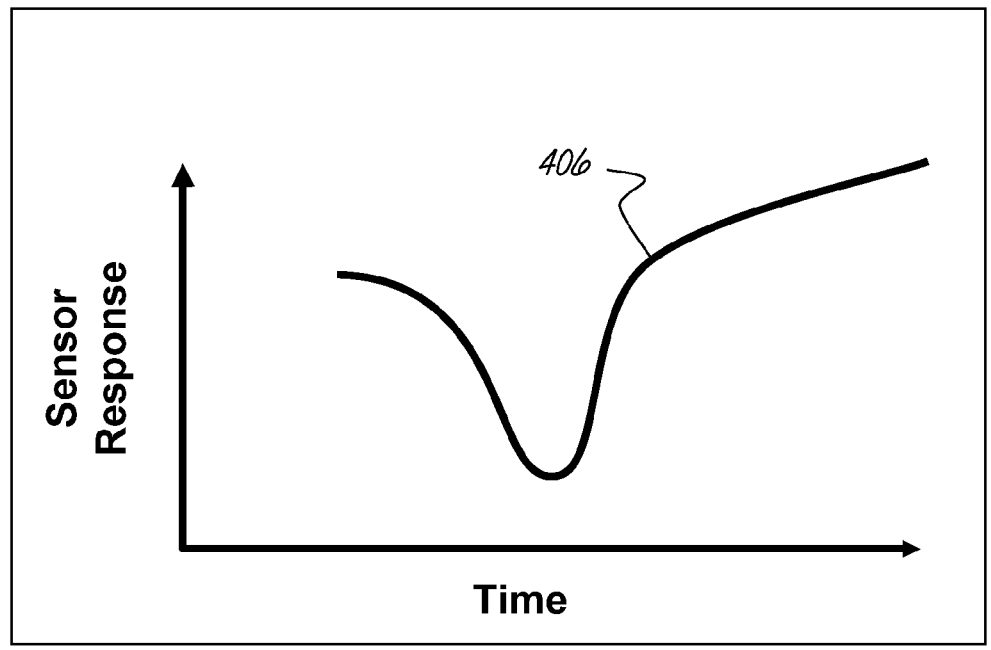
FIG. 24 is a graph showing the difference between the curves of FIG. 23.

With reference now to FIG. 23, result curves for a sequential differential analysis according to the invention for performing DTA are shown. In particular, FIG. 23 shows the raw results for sensor response versus time where curve 400 shows the analyte analysis cycle. The dotted line of curve 402 shows the reference analysis cycle. Both analysis cycles are performed using the same sensor cell or well, and the differential between the two curves is indicated by 404. Curve 406 of FIG. 24 represents the difference between curves 400 and 402 of FIG. 23. As is well known in the art, the sensor response for FIGS. 23 and 24 represents a temperature difference.

When doing differential thermal analysis (DTA) and applying a sequence of heating pulses to a cantilever and/or other sensor element, the analyte material collected on the sensor absorbs and/or releases heat that is detected by the sensor. If the first in a sequence of pulses is hot enough, the entirety of the analyte mass is removed in the analysis, and subsequent pulses can then provide a baseline corresponding to a "clean" sensor. However, if the first pulse is designed to be only hot enough (or energy enough) to remove only some of the analyte, then subsequent pulses will also be analyzing analyte mass. This technique can provide additional information about the analyte, possibly even information not available via the "one hot" pulse technique. For example, the lower-volatility component(s) of the analyte can remain on the sensor for the first pulse, while energy is absorbed by the higher-volatility component(s), which then desorb from the sensor. So the second, third, etc., pulses are then performed on a sub-set of the original analyte mass, representing a different overall composition, and by analyzing such subsets in this manner, a richer, more information-laden data set can be created, which can improve the performance of a pattern recognition algorithm used to identify the unknown analyte sample, and/or to identify various molecular components/mixtures in the sample.

FIG. 25 shows resulting curves for sequential analysis according to the invention performing DSC where power transferred to reference or analyte samples are graphed against temperature. Curve 500 represents the raw data from an analyte analysis cycle data run while curve 502 represents the raw data from a reference sample analysis cycle. Subtracting the two produces curve 504, which is the differential result. As previously described for the DTA test of FIG. 23, the DSC test of FIG. 25 may be performed according to one embodiment of the invention using a single sensor cell or well in a sequential manner.

In general, known systems perform DSC and DTA using two sample holders, one for the sample and one for a reference. The energy required to keep their temperatures the same, either in an isothermal mode or a temperature scanning mode, is the quantity measured. For example, if the sample melts, energy is supplied to the sample to keep its temperature the same as the reference; or, if the sample exothermally decomposes, less energy is supplied to the sample. In an alternative embodiment of the invention, this technique could be carried out with a pair of side-by-side resistive cantilevers. For example, the sample could be collected on both cantilevers and then one of the cantilevers could be cleaned off by applying heat using the integrated resistor (or even by performing a DTA or DSC test). This would create one "clean" reference and one sample-coated sensor, both in a nearly identical local environment. Here, the environmental fluctuations in temperature, humidity, pressure, etc., even vapors in the vicinity, would have equal effect on both sensors, thereby eliminating sensor responses to such environmental factors from the differential responses during DSC or DTA.

Multiple Scan Rate Selectivity Enhancement for DSC and DTA

Different biological molecules, like proteins, will unfold at different temperatures, and each different molecule type will sometimes also have a unique change in unfolding temperature as a function of heating scan/ramp rate. A first molecule type, for example, may melt at a 1.5× higher melting temperature when the heating rate is Y-times higher, however a second molecule type might melt at 1.8× higher temperature when the heating rate is Y-times higher. By performing multiple analyses quickly on multiple samples of the same analyte, multiple measurements can be taken at multiple heating rates providing additional information and thus improving the selectivity of the analysis overall.

Electrolysis as a Signal Booster for Thermal Analysis of Liquids

In one embodiment of the invention, resistance elements are formed in a cantilever or microbridge structure and are used to heat an analyte sample. Typically, a passivation layer may be formed over these heating structures such that they are electrically isolated from the analyte sample. Alternatively, by exposing a conductive heating structure such that it may interact with an analyte, a liquid analyte may undergo a form of electrolysis when voltage potentials exist across a heating structure, thereby conducting some amount of current through the analyte itself. When this occurs, the analyte sample has actually become part of the heating structure. Tests have shown that this functionality can boost a DSC or DTA signal resulting from a liquid analyte, in particular, containing a protein sample, whereby the electrolysis current in the liquid helps to instigate the denaturing process. As a result, the cantilever will have an "amplified" signal because more heat is applied to the sample than would otherwise be applied by heat transfer from a resistive heating element alone.

Application of Thermoelectric Devices

Figure 26:
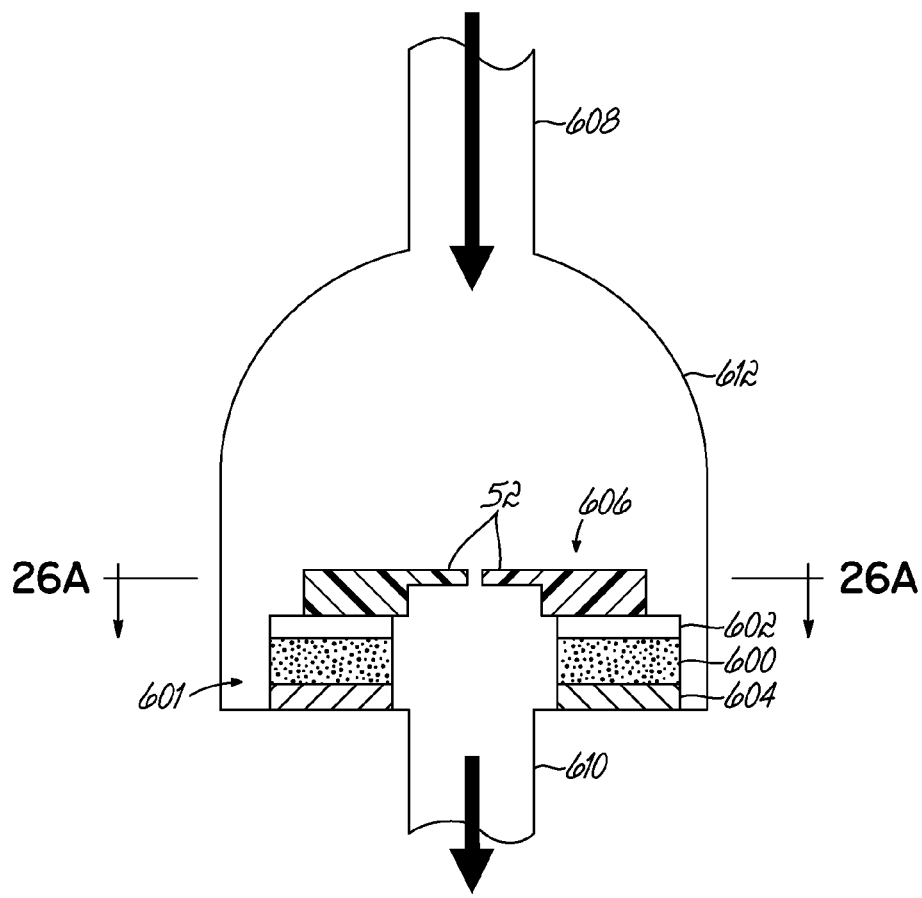
FIG. 26 is a cross-sectional view of a packaged sensor chip with a thermoelectric cooling device constructed in a doughnut shape.
Figure 26A:
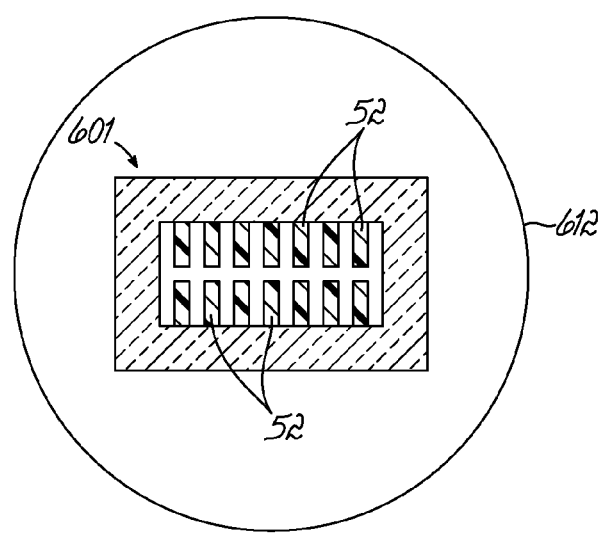
FIG. 26A is a cross-sectional view of FIG. 26 taken along line section 26A-26A.

With reference now to FIGS. 26 and 26A, thermoelectric cooling (TEC) devices 600, also known as TEC devices or Peltier devices, can be used for cooling or heating. FIG. 26 is a cross-section of a packaged sensor chip 601 in accordance with an embodiment of the invention, which utilizes TEC device 600, having both heating and cooling surfaces 604 and 602, respectively. Here, the TEC device 600 has been constructed in a "doughnut" shape such that for a vapor sensing or analysis application, vapors can pass through a cantilever array 606 and also through the TEC device 600 from an inlet 608 to an outlet 610 of package 612. Notice that the heating surface 604 of the TEC device 600 is in contact with the package 612, which in some embodiments is a metallic vapor containment vessel and therefore conducts heat well. The cooling surface 602 of the TEC device 600 is also in contact with the cantilever array 606. In this design, when current is supplied to the TEC, the TEC cooling surface 602 can lower the temperature of the cantilevers 52, thus promoting the adsorption of analyte molecules onto the surface of the cantilevers 52. At the same time, the heating surface 604 may be used to heat the sensor package 612 including the inlet 608 whereby analyte molecules are discouraged from attaching to the inner surfaces of the package 612 and inlet 608. As a result, a larger percentage of analyte molecules entering inlet 608 are available for analysis on the cantilevers 52. The TEC device 600 can also be controlled in a way to promote additional heating of a cantilever 52 when desired by reversing the direction of the current flow.

Alternatively, a thermoelectric cooler/heater (TEC) 600 can be used in conjunction with a MEMS-Based microsensor array 606 to conduct DSC or DTA by first using the TEC device 600 to control and enhance the collection of vapor phase analyte, and then supply heat in the analysis itself by:

1. Lowering the sensor chip temperature to enhance collection efficiency.
2. Modulating the sensor chip temperature to preferentially absorb a specific type of analyte, such as using low temps for all volatilities or higher temps to collect mostly low volatility species.
3. Providing controlled heating to ensure that DSC or/and DTA are performed at a consistent temperature from run to run for better/easier pattern recognition, including, in some instances, the benefit of avoiding temperature compensation in post-processing of sensor data.

Use of the TEC device 600 for heating ramps while performing DSC or DTA "frees up" the sensor chip's integrated resistor elements to serve solely as temperature sensor elements, instead of having to also, or only, be used as heating elements. As such, a very low-current (~0.1 mA) short-duration (~0.1 ms) pulse can be repeatedly applied to these resistors, which has little or no effect on their temperature as it is too short and small to cause self-heating throughout the analysis. Using the pulse height data (voltage measurements) gathered from temperature sensing resistors during the TEC-controlled heating/cooling programs is therefore a means of obtaining T vs. time plots used to differentiate analytes.

Reverse DSC and DTA

Using a thermoelectric cooler/heater, a two part DTA and/or DSC analysis can be performed using MEMS-based sensor devices as described herein. During Phase 1, the TEC device 600 is used to cool the sensor chip 601 in a programmed ramp. As the sensor chip cools in the immediate vicinity of analyte vapors or fluid, the analyte will begin collecting on the sensors (analyte can also be flowing past the sensor chip). Just as the temperatures at which rapid desorption and phase transitions can be observed when heating up, so too are these features observable when cooling down the sensor. So during the cooling period, one could observe condensation, solidification (freezing) and then as the subsequent heating phase (Phase 2) observe these same species as they melt and/or evaporate, and in some cases decompose.

Array of Cantilevers for Emersion in Liquid Samples

Figure 27:
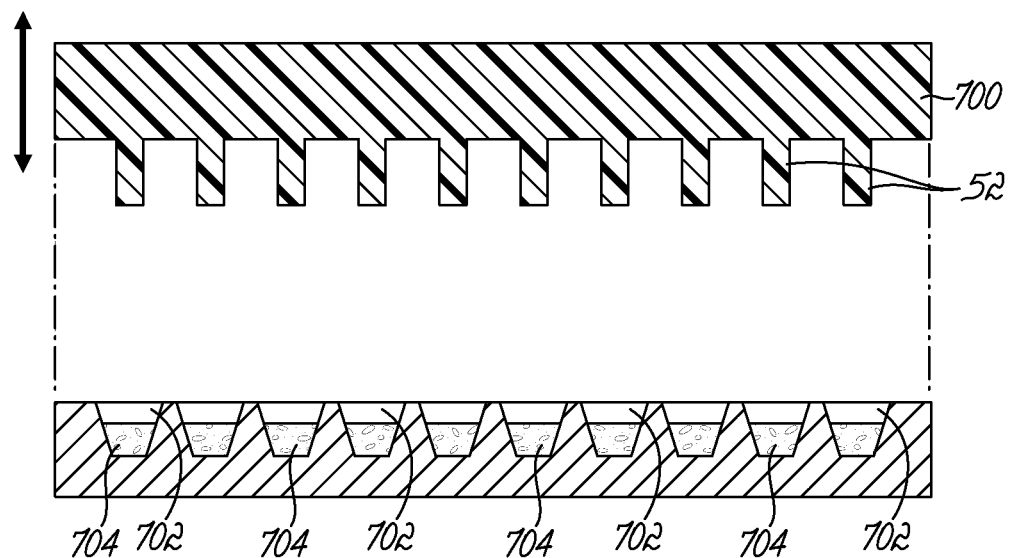
FIGS. 27 and 28 are cross-sectional views of a sensor array with cantilever shaped "tongues" for liquid thermal analysis of ultra-small liquid volumes in an open and closed position, respectively.
Figure 28:
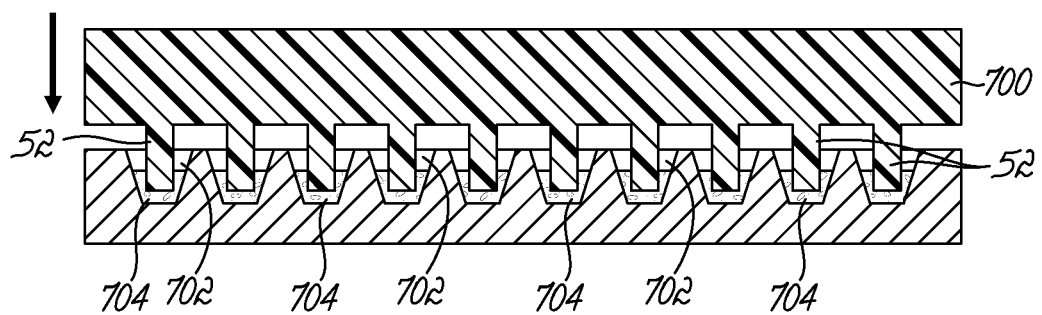

FIGS. 27 and 28 show an alternative embodiment to placing a liquid sample on a microsensor element, such as a cantilever or microbridge. In particular, an array 700 of cantilevers 52, shaped like "tongues," for liquid thermal analysis of ultra-small, even nanoliter scale, liquid volumes are shown. MEMS techniques, as known in the art, are used to fabricate the array 700 of cantilever thermal sensors 52 with a suspended silicon body and resistive heater/sensor paths integrated therein, as described above. The array 700 is moved either manually or robotically in different axes as appropriate, including vertically as shown by arrows. When aligned with the location of wells 702 containing the liquids 704 to be analyzed (e.g., buffer control, protein in buffer, water, cleaning agent(s), etc.), the cantilever array 700 is then submerged in the liquid samples 704 as shown in FIG. 28. Instead of bringing the liquid samples 704 to the cantilevers 52, the array 700 is placed or dipped into the wells 702 simultaneously for rapid analysis using, for example, multiplexers to interrogate the array 704 for Differential Scanning calorimetry DSC, DTA, and/or another type of molecular analysis. The device containing multiple analyte wells 702 can also be micro-fabricated using MEMS techniques known in the art for both precision and low-cost in volume.

Other Thermal Analysis Inventions

A micro-sensor cantilever or bridge structure for DSC and DTA can be calibrated by depositing a known material, such as pentaerythritol tetranitrate (PETN), and identifying the melting point feature in the plot. This point will move depending on the amount of material for some thermal measurements but the clearly visible feature will indicate that the bulk of the material is at a specific temperature, for example, the melting temperature of PETN.

The selectivity of an analysis system according to embodiments described herein can be increased by observing multiple decomposition paths of one analyte, for example, PETN or other thermally labile molecules. (This can also be helpful for molecules that can decompose differently in the presence of certain other chemicals). The temperature ramp of a collection surface or preconcentrator in an analysis system, which includes a collector or preconcentrator and an analysis instrument, can be varied from one measurement to another such that in one ramp a preconcentrator or collection surface is kept below the temperature or out of the chemical environment that causes the molecule to divide into two parts. In this way, the molecule will be passed from a preconcentrator to the sensors intact and will have a specific DTA or other analysis signature on the sensor. For example, PETN has a characteristic two-peak DTA signature. After the first ramp, a second sample of analyte or portion of the first sample can be ramped on the collection surface or in the preconcentrator to a temperature higher than the point where the molecule breaks into two or more pieces, or ramped in the presence of a chemical background that helps instigate this scission. In this case, the more volatile component that has broken loose may pass by the sensor and not stick as well, whereas the less volatile component will still adhere to the sensor. The analysis signal, for example, by DTA, will then look different in this case. For PETN, the higher the temperature the more the PETN DTA signal starts to become a one-peak signal. By combining the two signatures and the ramp rate, temperature, and condition information for both analyses into one data vector, more chemical information may be provided about the analyte and also more selectivity for the analysis instrument than just looking at the signature gathered from sample eluted at one ramp rate with one max ramp temperature.

Selective thermally induced (with or without catalyst) chemical vapor deposition can be performed on sensors for chemical and explosives detection. The deposition or growth of a byproduct on the sensor when heated to very high temperatures is in the range of 100° C. to 1200° C. can be indicative of the environment that the sensor is in. For example, heating the cantilever in this range in the presence of carbon can deposit carbon nanotubes on the sensor if it has a base catalyst material already on its surface. In another example, heating Indium on the sensor in the presence of oxygen can create and leave behind indium oxide. This principle can be applied to other chemical pairs such that analytes of interest react with a catalyst on the cantilever or the cantilever itself to create a deposition that can be measured by a change in thermal response or a change in mass.

By providing an analysis system using any combination of analysis methods described herein or otherwise known in the art, it is also possible to improve performance of a GC-MS analysis system by taking a small sample either separately or in-line with GC-MS to help select derivatizing reagents and system temperatures and protocols. The GC-MS often needs to be tuned for optimal performance depending on the type of analyte that is being analyzed and so for unknown samples, an analysis system as described herein can help direct the GC-MS operator to find the best settings more quickly by seeing that the sample is either low volatility, high volatility, or both. The analysis system can be configured to analyze just the low volatility, just the high volatility, or both, and can either be used to help set the protocol or help set the protocol and provide analysis information to be included in the GC-MS measurement information for added selectivity. This functionality can also be applied to other sensing systems like flame ionization detectors, PIDs, etc. An analysis system as described herein can also be coupled with a GC column as a stand-alone GC-sensor configuration.

A mode of DTA or DSC operation is possible where a first ramp can provide a first indication of the composition and or identity an analyte, while a second ramp can prove or disprove the hypothesis resulting from the first indication. For example, a second ramp can stop before the burn temperature identified in the first ramp and show that the signal remains endothermic. In a similar mode, the DTA analysis is actively used to establish a feedback control loop that would, for example, trigger a temperature hold if a large endothermic response was seen in order to monitor evaporation and melting. For another example, a small observed endothermic response can trigger a faster ramp to enhance an exothermic phase, and possible deflagration, before the sample evaporates too quickly given a small amount of available mass.

For analytical labs and potentially other application as well, it is possible to dissolve a sample in solution and then deposit a precise amount on a cantilever or microbridge sensor for analysis. Analysis could be done during injection, during evaporation of a solvent, or after the solvent has evaporated and left behind a solid sample. This can also be done with liquid samples for life science DSC and protein studies, for example. Finally, with two or more injectors, one could inject a liquid or solid solution of one type and another injector could inject a reactant liquid or solid, so as to study the interaction between the two on one sensor either in liquid or solid form. This could enable ITC for life science on a single cantilever or bridge sensor.

The foregoing description of preferred embodiments of the present invention has been provided for the purposes of illustration and description. It is not intended to be exhaustive or to limit the invention to the precise forms disclosed. Many modifications and variations will be apparent to one of ordinary skill in the relevant arts, while remaining within the scope of the appended claims. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the appended claims and their legal equivalents.

The invention claimed is:

1. A sensor device for at least one of differential scanning calorimetry and differential thermal analysis of an analyte, the sensor device comprising:
    an array comprising a plurality of sensor cells arranged in at least one row and in at least one column, each sensor cell configured to receive analyte for analysis thereof, each sensor cell comprising:
        a heating element configured to heat at least one of the sensor cell or the analyte; and
        a temperature sensor element configured to sense a temperature response of at least one of the sensor cell and the analyte; and
    a controller configured to:
        drive the heating element of at least one sensor cell according to a first temperature ramp cycle while analyte is present on the at least one sensor cell;
        drive the heating element of the at least one sensor cell according to a second temperature ramp cycle to clean the at least one sensor cell; and
        drive the heating element of the cleaned at least one sensor cell according to a third temperature ramp cycle to obtain reference temperature data; and
    a processor configured to determine a difference between an output signal from the temperature sensor of the at least one sensor cell during the first temperature ramp cycle and an output signal from the temperature sensor of the at least one sensor cell during the third temperature ramp cycle.

2. The sensor device of claim 1, wherein each sensor cell includes a cantilever having an unsupported free end or microbridge structure comprising a bridge support structure.

3. The sensor device of claim 1, wherein each sensor cell includes a microbridge structure having a suspended platform.

4. The sensor device of claim 3, wherein the platform includes the heating element and temperature sensor element.

5. The sensor device of claim 1, wherein each sensor cell includes a cantilever having a doped electrically conductive portion extending along opposing edges of the cantilever and extending from a fixed end thereof toward a free end thereof.

6. The sensor device of claim 5, wherein each cantilever comprises a central portion between the electrically conductive portion, the central portion having a lower electrical conductivity than the electrically conductive portion.

7. The sensor device of claim 1, wherein each sensor comprises a cantilever, at least one cantilever comprising an electrically conductive portion along opposing edges of the at least one cantilever, the at least one cantilever comprising a slot located proximate a base of the at least one cantilever between the electrically conductive portion.

8. The sensor device of claim 1, wherein the controller is configured to drive the heating element of the at least sensor cell by providing power to a column associated with the at least sensor cell and a row associated with the at least one sensor cell.

9. The sensor device of claim 1, wherein each of the heating elements and each the temperature sensor elements comprise silicon, polysilicon, platinum, nichrome, tungsten, or titanium tungsten.

10. The sensor device of claim 1, wherein:
    the controller is configured to adjust a power applied to the at least one sensor cell to maintain a desired temperature during each of the first temperature ramp cycle and the third temperature ramp cycle; and
    the output signal from the temperature sensor of the at least one sensor cell comprises a sensor power required to maintain a temperature of the at least one sensor cell.

11. The sensor device of claim 1, wherein the processor is configured to sum an output from a plurality of the sensor cells to produce a summed response.

12. The sensor device of claim 1, wherein the processor is configured to determine a temperature of the at least one sensor cell during each of the first temperature ramp cycle and the third temperature ramp cycle as a function of time.

13. The sensor device of claim 1, wherein the processor is configured to determine a power required to maintain constant temperature of the at least one sensor cell during the first temperature ramp cycle and during the third temperature ramp cycle.

14. The sensor device of claim 1, wherein the plurality of sensor cells comprise a plurality of rectangular-shaped cantilevers and a plurality of triangular-shaped cantilevers.

15. The sensor device of claim 1, wherein the plurality of sensor cells comprise a plurality of cantilevers arranged in an alternating pattern, wherein a free end of each cantilever is proximate a fixed end of an adjacent cantilever and wherein the fixed end of the cantilever is adjacent a free end of the adjacent cantilever, adjacent cantilevers separated by a gap having a serpentine shape.

16. The sensor device of claim 1, wherein at least one sensor cell comprises a cantilever comprising alternating regions of doped silicon and undoped silicon between a doped electrically conductive portion extending along opposing edges thereof.

17. The sensor device of claim 16, wherein the alternating regions of doped silicon and undoped silicon exhibit are spaced from adjacent regions by varying distances.

18. The sensor device of claim 1, wherein the at least one sensor cell comprises a cantilever having a plurality of holes therein.

19. The sensor device of claim 18, wherein the plurality of holes are arranged in a pattern of rows.

20. The sensor device of claim 19, wherein the adjacent rows are spaced at different distances from each other.

* * * * *

UNITED STATES PATENT AND TRADEMARK OFFICE
CERTIFICATE OF CORRECTION

PATENT NO. : 9,625,401 B2
APPLICATION NO. : 14/425423
DATED : April 18, 2017
INVENTOR(S) : Ralph G. Whitten et al.

It is certified that error appears in the above-identified patent and that said Letters Patent is hereby corrected as shown below:

In the Specification
Column 6, Line 30, change "line section" to --section line--

Signed and Sealed this
Twenty-third Day of January, 2018

Joseph Matal
*Performing the Functions and Duties of the
Under Secretary of Commerce for Intellectual Property and
Director of the United States Patent and Trademark Office*